US012037649B2

(12) United States Patent
Paquette et al.

(10) Patent No.: US 12,037,649 B2
(45) Date of Patent: Jul. 16, 2024

(54) MULTIPLEX DETECTION OF VULVOVAGINAL CANDIDIASIS, TRICHOMONIASIS AND BACTERIAL VAGINOSIS

(71) Applicant: Becton, Dickinson and Company, Franklin Lakes, NJ (US)

(72) Inventors: Nancy Paquette, Quebec (CA); Marie-Helene Tremblay, Quebec (CA); Simon Tremblay, Quebec (CA); Roseline Therrien, Quebec (CA); Marie-Christine Fortin, Quebec (CA); Lucile Belley-Montfort, Quebec (CA); Dany Cantin, Quebec (CA); Celine Roger-Dalbert, Quebec (CA)

(73) Assignee: Becton, Dickinson and Company, Franklin Lakes, NJ (US)

( * ) Notice: Subject to any disclaimer, the term of this patent is extended or adjusted under 35 U.S.C. 154(b) by 242 days.

(21) Appl. No.: 17/370,923

(22) Filed: Jul. 8, 2021

(65) Prior Publication Data
US 2021/0332421 A1    Oct. 28, 2021

Related U.S. Application Data

(62) Division of application No. 15/567,051, filed as application No. PCT/US2016/028433 on Apr. 20, 2016, now Pat. No. 11,098,376.

(60) Provisional application No. 62/279,220, filed on Jan. 15, 2016, provisional application No. 62/152,754, filed on Apr. 24, 2015.

(51) Int. Cl.
| *C12Q 1/6893* | (2018.01) |
| *C12Q 1/68* | (2018.01) |
| *C12Q 1/6883* | (2018.01) |
| *C12Q 1/689* | (2018.01) |
| *C12Q 1/6895* | (2018.01) |

(52) U.S. Cl.
CPC .............. *C12Q 1/689* (2013.01); *C12Q 1/68* (2013.01); *C12Q 1/6883* (2013.01); *C12Q 1/6893* (2013.01); *C12Q 1/6895* (2013.01)

(58) Field of Classification Search
CPC ............................ C12Q 1/6893; C12Q 1/6895
See application file for complete search history.

(56) References Cited

U.S. PATENT DOCUMENTS

| 3,649,454 A | 3/1972 | Isono et al. |
| 3,716,452 A | 2/1973 | Kitamura et al. |
| 4,683,195 A | 7/1987 | Mullis et al. |
| 4,683,202 A | 7/1987 | Mullis |
| 4,800,159 A | 1/1989 | Mullis et al. |
| 4,988,617 A | 1/1991 | Landegren et al. |
| 5,130,238 A | 7/1992 | Malek et al. |
| 5,185,242 A | 2/1993 | Keating et al. |
| 5,399,491 A | 3/1995 | Kacian et al. |
| 5,427,930 A | 6/1995 | Birkenmeyer et al. |
| 5,455,166 A | 10/1995 | Walker |
| 5,849,478 A | 12/1998 | Cashman |
| 5,854,033 A | 12/1998 | Lizardi |
| 6,410,278 B1 | 6/2002 | Notomi et al. |
| 6,977,148 B2 | 12/2005 | Dean et al. |
| 7,494,771 B2 | 2/2009 | Picard et al. |
| 7,625,704 B2 | 12/2009 | Fredricks et al. |
| 8,067,207 B2 | 11/2011 | Bergeron et al. |
| 2007/0178495 A1 | 8/2007 | Fredricks et al. |
| 2013/0288988 A1 | 10/2013 | Cartwright et al. |
| 2013/0316922 A1 | 11/2013 | Balashov et al. |
| 2014/0030710 A1 | 1/2014 | Stevens |
| 2014/0127684 A1 | 5/2014 | Bergeron et al. |
| 2014/0302500 A1 | 10/2014 | Getman et al. |
| 2015/0104805 A1 | 4/2015 | Mc Millian |

FOREIGN PATENT DOCUMENTS

| WO | WO2003008636 | 1/2003 |
| WO | WO2008062136 | 5/2008 |
| WO | WO2010083274 | 7/2010 |
| WO | WO2011103274 | 8/2011 |
| WO | WO2012149034 | 11/2012 |

OTHER PUBLICATIONS

Amsel et al., "Nonspecific vaginitis: Diagnostic criteria and microbial and epidemiologic associations," Am. J. Med. 1983, 74(1), 14-22.
Cartwright et al., "Development and Validation of a Semiquantitative, Multitarget PCR Assay for Diagnosis of Bacterial Vaginosis," Journal of Clinical Microbiology 2012, 50(7), 2321-2329.
De Backer et al., "Quantitative determination by real-time PCR of four vaginal *Lactobacillus* species, *Gardnerella vaginalis* and *Atopobium vaginae* indicates an inverse relationship between L. *Gasseri* and L. *Iners*," BMC Microbiology 2007, 7(115), 1-13.
Examination Report dated Apr. 28, 2020 in Australian Patent Application No. 2016252551.
Examination Report dated Jun. 10, 2020 in European Patent Application No. 16783760.8.
Examination Report dated Apr. 14, 2021 in European Patent Application No. 16783760.8.
Examination Report dated Nov. 5, 2019 in Australian Patent Application No. 2016252551.
Examination Report dated Apr. 21, 2021 in Australian Patent Application No. 2020205314.
Extended European Search Reported dated Nov. 28, 2018 in European Patent Application No. 16783760.8.

(Continued)

*Primary Examiner* — Diana B Johannsen
(74) *Attorney, Agent, or Firm* — Sheppard, Mullin, Richter & Hampton LLP

(57) ABSTRACT

Methods and compositions for detection of vulvovaginal candidiasis (VVC), trichomoniasis and bacterial vaginosis (BV) are disclosed herein. In some embodiments, the presence or absence of VVC-associated *Candida*, *Trichomonas vaginalis*, and a plurality of BV-related bacteria in a sample is determined using multiplex nucleic acid-based testing methods.

19 Claims, No Drawings

Specification includes a Sequence Listing.

(56) References Cited

OTHER PUBLICATIONS

Ezaki et al., "Achromopeptidase for lysis of anaerobic gram-positive cocci," J Clin Microbiol. 1982, 16(5), 844-846.
Final Office Action dated Jun. 18, 2020 in U.S. Appl. No. 15/567,051.
Fredricks et al., "Targeted PCR for Detection of Vaginal Bacteria Associated with Bacterial Vaginosis," J. Clin. Microbiol. 2007, 45(10), 3270-3276.
International Search Report and Written Opinion dated Aug. 11, 2016 in PCT Application No. PCT/US2016/028433.
Lizardi et al., "Exponential Amplification of Recombinant—RNA Hybridization Probes" Bio/Technology 1988, 6, 1197-1202.
Menard et al., "Molecular quantification of Gardnerella vaginalis and Atopobium vaginae loads to predict bacterial vaginosis," Clin Infect Dis. 2008, 47(1), 33-43.
Mullis et al., "Specific synthesis of DNA in vitro via a polymerase-catalyzed chain reaction," Methods Enzymol. 1987, 155, 335-350.
Non-Final Office Action dated Dec. 23, 2019 in U.S. Appl. No. 15/567,051.
Non-Final Office Action dated Dec. 28, 2020 in U.S. Appl. No. 15/567,051.
Notice of Allowance dated Jun. 15, 2021, in U.S. Appl. No. 15/567,051.
Notice of Allowance dated Jul. 21, 2021, in U.S. Appl. No. 15/567,051.
Nugent et al., "Reliability of diagnosing bacterial vaginosis is improved by a standardized method of gram stain interpretation.," Journal of Clinical Microbiology 1991, 29(2), 297-301.
Office Action dated Jan. 7, 2020 in Brazilian Patent Application No. BR112017022379-1.
Paule et al., "Direct Detection of *Staphylococcus aureus* from Adult and Neonate Nasal Swab Specimens Using Real-Time Polymerase Chain Reaction," The Journal of Molecular Diagnostics 2004, 6(3), 191-196.
Pleckaityte et al., "Genetic and biochemical diversity of Gardnerella vaginalis strains isolated from women with bacterial vaginosis," FEMS Immunol Med Microbiol 2012, 65, 69-77.
Restriction Requirement dated Jul. 25, 2017 in U.S. Appl. No. 15/567,051.
Sha et al., "Utility of Amsel criteria, Nugent score, and quantitative PCR for Gardnerella vaginalis, *Mycoplasma hominis*, and *Lactobacillus* spp. for diagnosis of bacterial vaginosis in human immunodeficiency virus-infected women," J Clin Microbiol. 2005, 43(9), 4607-12.
Shipitsyna et al., "Composition of the Vaginal Microbiota in Women of Reproductive Age—Sensitive and Specific Molecular Diagnosis of Bacterial Vaginosis is Possible?," Plos One 2013, 8(4), e60670.
Zariffard et al., "Detection of bacterial vaginosis-related organisms by real-time PCR for Lactobacilli, Gardnerella vaginalis and Mycoplasma hominis," FEMS Immunol Med Microbiol. 2002, 34(4), 277-81.
Zozaya-Hinchliffe et al., "Quantitative PCR assessments of bacterial species in women with and without bacterial vaginosis," J Clin Microbiol. 2010, 48(5), 1812-9.
Technical Examination Report dated Oct. 10, 2023 in Brazilian Patent Application No. BR1120170223791.
Examination Report dated Dec. 23, 2021 in European Patent Application No. 16783760.8.
Examination Report dated Nov. 22, 2022 in Australian Patent Application No. 2021286250.
Notice of Allowance dated Jun. 22, 2020, in Australian Patent Application No. 2016252551.
Notice of Allowance dated Oct. 5, 2021, in Australian Patent Application No. 2020205314.
Notice of Allowance dated Feb. 18, 2022, in Australian Patent Application No. 2020205314.
Notice of Allowance dated Dec. 22, 2022, in Australian Patent Application No. 2021286250.
Notice of Allowance dated Dec. 22, 2022 in European Patent Application No. 16783760.8.
Office Action dated Jan. 19, 2022 in Canadian Patent Application No. 2,982,467.
Office Action dated Dec. 8, 2022 in Canadian Patent Application No. 2,982,467.
Office Action dated Jun. 21, 2022 in Korean Patent Application No. 10-2017-7032958.
Office Action dated Dec. 22, 2022 in Korean Patent Application No. 10-2017-7032958.
Extended European Search Reported dated Mar. 3, 2023 in European Patent Application No. 22200785.8.
Notice of Allowance dated Jun. 19, 2023 in Korean Patent Application No. 10-2017-7032958.
Rad, et al. "Identification of Candida Species Associated with Vulvovaginal Candidiasis by Multiplex PCR", Infectious Diseases in Obstetrics and Gynecology, 2012, vol. 2012, 1-5.
Savochkina, et al., "The Development of Technique of Diagnostic of Vuvlvovaginal Candidiasis Based on Quantitative Multiplex Polymerase Chain Reaction", KLIN LAB DIAGN, 2015, 60(4), 55-62.
Office action Dated Feb. 29, 2024 in Brazilian Patent Application No. BR112017022379-1.
Office Action dated Apr. 23, 2024 in Korean Patent Application No. 10-2023-7026463.

SEQUENCE LISTING

```
<160> NUMBER OF SEQ ID NOS: 182

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ccctatccgc tcctgatacc                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ccaaatatct gcgcatttca                                          20

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
tcccctacca gactcaagcc tgc                                      23

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
gcggctagat aagtgtgatg ttt                                      23

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
ctctccagca ctcaagctaa a                                        21
```

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 6
caaggcttaa ccttggggtt cattacaa                                    28

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
gatgccaaca gtatccgtcc g                                           21

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
cctctccgac actcaagttc ga                                          22

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
taccgtaaga gaaagccacg g                                           21

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
gccaacgatg atcgcgtat                                              19

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
gccaataatg accgcgtat                                              19

<210> SEQ ID NO 12
<211> LENGTH: 19
<212> TYPE: DNA
<213> ORGANISM: Artificial Sequence
<220> FEATURE:

```
<223> OTHER INFORMATION: Synthetic oligonucleotide

<400> SEQUENCE: 12
agccgttcac tgcggaagt                                              19

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
acagcacttt cgccgcc                                                17

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
ttaaaaggcg gcgtaagc                                               18

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 15
gccagttact acctctatc                                              19

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
aagtctgatg gagcaacgcc                                             20

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
gaagattctg gcaagatcaa gga                                         23

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
acgacaatgc agcggatgt                                              19
```

```
<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 19
atcctccgca actacccacg cca                                              23

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
cgaacaattg actgaaggtt tg                                               22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
cggacttcaa gaactttgga ga                                               22

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
cttgtaagtt cgaagaattg ttgga                                            25

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
ccaccaaagg gttgtgac                                                    18

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 24
cagcatcacc ggatttgac                                                   19

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide
```

```
<400> SEQUENCE: 25
cggacttgat gaattttggt tca                                          23

<210> SEQ ID NO 26
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 26
tgcttgtaaa ttcgacactt tggttg                                       26

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
gcagcttcct tcaatgctca a                                            21

<210> SEQ ID NO 28
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 28
atcaccagac ttgacag                                                 17

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
catgtaagtt cgacgaatta atcga                                        25

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
ggcatggagg ttgtcccatt tgtg                                         24

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
ggatctagcc gtgtgcccgc t                                            21

<210> SEQ ID NO 32
<211> LENGTH: 32
```

```
<212> TYPE: DNA
<213> ORGANISM: Artificial Sequence
<220> FEATURE:
<223> OTHER INFORMATION: Synthetic oligonucleotide

<400> SEQUENCE: 32
ttgatgcctc ttcacattgc tccacctttc ct                                    32

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 33
gttaggtcag gagttaaatc tg                                               22

<210> SEQ ID NO 34
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 34
tcatggccca gaagacc                                                     17

<210> SEQ ID NO 35
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 35
tcgtggccca gaaggcc                                                     17

<210> SEQ ID NO 36
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 36
ccctggtagt cctagct                                                     17

<210> SEQ ID NO 37
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 37
ccctggtagt cctagcc                                                     17

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
```

-continued cggcacggaa agtataatct                20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ggtgaagcag tggaaacact                20

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 40
ttcgcttctg ctcgcgca                18

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41
gcagcccagg acataagg                18

<210> SEQ ID NO 42
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 42
attcgcttct gctcgcgca                19

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
gcagggacga ggccgcaa                18

<210> SEQ ID NO 44
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 44
tcatggccca gaagacc                17

<210> SEQ ID NO 45
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 45
cggattcatt gggcgtaaa                                                19

<210> SEQ ID NO 46
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 46
cgcctcagcg tcagt                                                    15

<210> SEQ ID NO 47
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 47
cggattcatt gggcgtaaa                                                19

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
acacctagtg tccatcgttt a                                             21

<210> SEQ ID NO 49
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 49
ccttcgggtt gtaaaccg                                                 18

<210> SEQ ID NO 50
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 50
cgcctcagcg tcagt                                                    15

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
aggcggctag ataagtgtga                                               20
```

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 52
tcctctccag cactcaagct aa                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 53
ttaaccttgg ggttcattac aa                                              22

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
aattcagtct cctgaatcgt caga                                            24

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
aggcggctag ataagtgtga                                                 20

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56
cgtgtaggcg gctagataag tg                                              22

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 57
gaatacttat tgtgttaact gcgc                                            24

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 58
aagttcgaca gtttccgtcc cctc                                              24

<210> SEQ ID NO 59
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 59
ggcggcgaaa gtgctgta                                                     18

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 60
caagctcggc atgttatcca t                                                 21

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 61
ggaaacgggt ggtaatgctg g                                                 21

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
cgaagcctag gtgggccatt                                                   20

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
ttactggtgt atcactgtaa gg                                                22

<210> SEQ ID NO 64
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 64
ccgtcacagg ctgaacagt                                                    19

<210> SEQ ID NO 65

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 65
ccagaatttg atggataaca tgcc                                           24

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
atggacaata tgccaagcct                                                20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
ttcactgcgg aagttacaga                                                20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
ttaactgcgg aagtaacgga                                                20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
ttaactgctg aagtaacgga                                                20

<210> SEQ ID NO 70
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 70
acagcactct cgccgcc                                                   17

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 71
```

```
gatagaggta gtaactggcc ttta                                              24

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 72
ctttgtatct ctacaaatgg cacta                                             25

<210> SEQ ID NO 73
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 73
cgagcttgcc tagatgaatt tg                                                22

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
ctctagacat gcgtctagtg                                                   20

<210> SEQ ID NO 75
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 75
gatttacttc ggtaatgacg ttagga                                            26

<210> SEQ ID NO 76
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 76
agctgatcat gcgatctgct ttc                                               23

<210> SEQ ID NO 77
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 77
gcctatagaa attcttcgga atggaca                                           27

<210> SEQ ID NO 78
<211> LENGTH: 24
<212> TYPE: DNA
```

<213> ORGANISM: Artificial Sequence
<220> FEATURE:
<223> OTHER INFORMATION: Synthetic oligonucleotide

<400> SEQUENCE: 78
caaatggtat cccagactta aggg        24

<210> SEQ ID NO 79
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 79
gtcgagcgag cttgccta        18

<210> SEQ ID NO 80
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 80
gaactaacag atttacttcg gtaatg        26

<210> SEQ ID NO 81
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 81
aaactctaga catgcgtcta gt        22

<210> SEQ ID NO 82
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 82
gtttccaaat ggtatcccag a        21

<210> SEQ ID NO 83
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 83
gcctagatga atttggtgct t        21

<210> SEQ ID NO 84
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 84
cgagcttgcc tatagaaatt ctt        23

<210> SEQ ID NO 85
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 85
gaactaacag atttacttcg gtaatg                                          26

<210> SEQ ID NO 86
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 86
aaactctaga catgcgtcta gt                                              22

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 87
gtttccaaat ggtatcccag a                                               21

<210> SEQ ID NO 88
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 88
actagacgca tgtctagagt tt                                              22

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 89
tgcattagct agttggtaag gtaac                                           25

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
acattgggac tgagacacgg                                                 20

<210> SEQ ID NO 91
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 91
aggcttacca aggcgatgat                                           20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
cggcttacca aggcaatgat                                           20

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 93
tgcattagct agttggtaag gtaac                                     25

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
acattgggac tgagacacgg                                           20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
aggcttacca aggcgatgat                                           20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
cggcttacca aggcaatgat                                           20

<210> SEQ ID NO 97
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 97
cgagcttgcc tagatgaatt tg                                        22

<210> SEQ ID NO 98
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 98
gcctatagaa attcttcgga atggaca         27

<210> SEQ ID NO 99
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 99
gatttacttc ggtaatgacg ttagga          26

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ctctagacat gcgtctagtg                 20

<210> SEQ ID NO 101
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 101
caaatggtat cccagactta aggg            24

<210> SEQ ID NO 102
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 102
agctgatcat gcgatctgct ttc             23

<210> SEQ ID NO 103
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 103
cggcggatgg gtgagtaac                  19

<210> SEQ ID NO 104
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 104
cggcggatgg gtgagtaac                                              19

<210> SEQ ID NO 105
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 105
ccaagagact gggataacac ctg                                         23

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
cgcatctgct aaggatgttg                                             20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
cagcaatctt ttcgccaact                                             20

<210> SEQ ID NO 108
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 108
tgcaactatt tctgcagcag atcc                                        24

<210> SEQ ID NO 109
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 109
caggcttggc atattgtcca t                                           21

<210> SEQ ID NO 110
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 110
cccaggtgct cttttccgtg ctga                                        24

<210> SEQ ID NO 111
<211> LENGTH: 24

```
<212> TYPE: DNA
<213> ORGANISM: Artificial Sequence
<220> FEATURE:
<223> OTHER INFORMATION: Synthetic oligonucleotide

<400> SEQUENCE: 111
cccaggtgcg ctgttccgcg ctga                                              24

<210> SEQ ID NO 112
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 112
ggcggcgaaa gtgctgtc                                                     18

<210> SEQ ID NO 113
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 113
ttcagcgccc aaccaagagc tctgt                                             25

<210> SEQ ID NO 114
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 114
ttaagcatcc aactaagagc tctgt                                             25

<210> SEQ ID NO 115
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 115
tcttcggaat ggacatagat acaagcta                                          28

<210> SEQ ID NO 116
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 116
atccgccgct cgcttt                                                       16

<210> SEQ ID NO 117
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 117
```

```
cgggtgggaa attcggt                                                  17

<210> SEQ ID NO 118
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 118
caatgatcgg tatcgggt                                                 18

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 119
cagcttgtag taaagaatta ctcac                                         25

<210> SEQ ID NO 120
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 120
ttcgcatatt gcactaaata g                                             21

<210> SEQ ID NO 121
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 121
ttcgcatatt gcactaaaca g                                             21

<210> SEQ ID NO 122
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 122
caacgccaac gaagacaag                                                19

<210> SEQ ID NO 123
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 123
ccagctttgt ttgcatcaa                                                19

<210> SEQ ID NO 124
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 124
aaagccgatg gtagtagaaa actgc                                      25

<210> SEQ ID NO 125
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 125
ttgaacatct ccagtttcaa aggt                                       24

<210> SEQ ID NO 126
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 126
gttggcgttg gcaatagctc tg                                         22

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 127
cgcctcttga tggtgatgat                                            20

<210> SEQ ID NO 128
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 128
tccggtatca cctggctc                                              18

<210> SEQ ID NO 129
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 129
cgttcgtact agagttgtgt tgttttggat                                 30

<210> SEQ ID NO 130
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 130
gaggctgtga tgtgtgctgt tgaccag                                    27
```

```
<210> SEQ ID NO 131
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 131
aggcttgctc tttgtcgggc gagcgaacg                              29

<210> SEQ ID NO 132
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 132
caggtcacag agatttcatc aag                                    23

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
gaaattcggt ggtacgctcc                                        20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
gaaattcggt ggtactctcc                                        20

<210> SEQ ID NO 135
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 135
gttgtgactc tttcaatgcc caa                                    23

<210> SEQ ID NO 136
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 136
gttgtgactc tttcaacgct caa                                    23

<210> SEQ ID NO 137
<211> LENGTH: 23
<212> TYPE: DNA
<213> ORGANISM: Artificial Sequence
<220> FEATURE:
<223> OTHER INFORMATION: Synthetic oligonucleotide
```

```
<400> SEQUENCE: 137
gatgtgactc cttcaatgct caa                                          23

<210> SEQ ID NO 138
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 138
gtaagccaac aaagcgtgtt ctc                                          23

<210> SEQ ID NO 139
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 139
gaaagccaat agagcgtgtt ctc                                          23

<210> SEQ ID NO 140
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 140
gatcggtatc gggtgcttg                                               19

<210> SEQ ID NO 141
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 141
gatcggtatc gggttcttg                                               19

<210> SEQ ID NO 142
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 142
cagcgtcacc ggatttgac                                               19

<210> SEQ ID NO 143
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 143
tgattattgc tggtgg                                                  16

<210> SEQ ID NO 144
```

```
<210> SEQ ID NO 144
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 144
tgcttgtaaa ttcgacactt tg                                          22

<210> SEQ ID NO 145
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 145
tgtaaattcg acaccttggt tga                                         23

<210> SEQ ID NO 146
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 146
ttgtaaattc gacactttgg ttg                                         23

<210> SEQ ID NO 147
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 147
cgacactttg attgaaaaga ttgac                                       25

<210> SEQ ID NO 148
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 148
gggtttgctt gaaagacggt a                                           21

<210> SEQ ID NO 149
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 149
cgtggtaact tattttaagc g                                           21

<210> SEQ ID NO 150
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 150
```
gggtttggtg ttgagcgata c                                    21

<210> SEQ ID NO 151
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 151
ttgaagatat acgtggtgga cgtta                                 25

<210> SEQ ID NO 152
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 152
gcttaagttc agcgggtagt ccta                                  24

<210> SEQ ID NO 153
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 153
ggagtttgta ccaatgagtg gaaa                                  24

<210> SEQ ID NO 154
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 154
acctaagcca ttgtcaaagc gatcccg                               27

<210> SEQ ID NO 155
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 155
tggccaccat ttatttcata actttgacc                             29

<210> SEQ ID NO 156
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 156
ctccgccttt ctttcaagca aacccag                               27

<210> SEQ ID NO 157
<211> LENGTH: 16
<212> TYPE: DNA

```
<213> ORGANISM: Artificial Sequence
<220> FEATURE:
<223> OTHER INFORMATION: Synthetic oligonucleotide

<400> SEQUENCE: 157
ggcaacggct gggaat                                                    16

<210> SEQ ID NO 158
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 158
agcaacggct gggaat                                                    16

<210> SEQ ID NO 159
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 159
caatgatcgg tatcgggt                                                  18

<210> SEQ ID NO 160
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 160
taaagcctca ccacgatttt gacac                                          25

<210> SEQ ID NO 161
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 161
cccaaaaatg gccgtaagta tg                                             22

<210> SEQ ID NO 162
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 162
ctgcttgaaa gaaatatcgg agac                                           24

<210> SEQ ID NO 163
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 163
cgactggttg acgataatca gaggagatgg g                                   31
```

<210> SEQ ID NO 164
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 164
acccaccaaa ggctgct                                                17

<210> SEQ ID NO 165
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 165
cgacccacca aaggctgct                                              19

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
actgtcacac cgcccacatt                                             20

<210> SEQ ID NO 167
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 167
atagagtagc tcggtccc                                               18

<210> SEQ ID NO 168
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 168
tagtgatcgg tatcgagtt                                              19

<210> SEQ ID NO 169
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 169
cggtatcgag tttccatg                                               18

<210> SEQ ID NO 170
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 170
ccaaagttgt acaagcaagt acca                                          24

<210> SEQ ID NO 171
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 171
gagccacggt aaagaataca ca                                            22

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 172
tttaaagtga cccggatacc                                               20

<210> SEQ ID NO 173
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 173
ctttggatgg tcttcaacag a                                             21

<210> SEQ ID NO 174
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 174
atcaccagac ttgacgg                                                  17

<210> SEQ ID NO 175
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 175
agtctgttga agaccatcca                                               20

<210> SEQ ID NO 176
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 176
atgtaagttc gacgaattaa tc                                            22

```
<210> SEQ ID NO 177
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 177
tctggcaaga tcaaggacat                                               20

<210> SEQ ID NO 178
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 178
gaagattctg gcaagatca                                                19

<210> SEQ ID NO 179
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 179
catctgtaac gacaatgcag c                                             21

<210> SEQ ID NO 180
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 180
gacaatgcag cggat                                                    15

<210> SEQ ID NO 181
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 181
aactacccac gccaggacat                                               20

<210> SEQ ID NO 182
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 182
ccgcaactac ccacgcca                                                 18
```

MULTIPLEX DETECTION OF VULVOVAGINAL CANDIDIASIS, TRICHOMONIASIS AND BACTERIAL VAGINOSIS

RELATED APPLICATIONS

The present application is a divisional application of U.S. patent application Ser. No. 15/567,051 filed on Oct. 16, 2017, which is the U.S. National Phase under 35 U.S.C. § 371 of International Patent Application No. PCT/US2016/028433 entitled "Multiplex Detection of Vulvovaginal Candidiasis, Trichomoniasis and Bacterial Vaginosis," filed on Apr. 20, 2016, which claims priority under 35 U.S.C. § 119(e) to U.S. Provisional Application No. 62/152,754, filed on Apr. 24, 2015; and U.S. Provisional Application No. 62/279,220, filed on Jan. 15, 2016. The content of these related applications is herein expressly incorporated by reference in its entirety.

REFERENCE TO SEQUENCE LISTING

The present application is being filed along with a Sequence Listing in electronic format. The Sequence Listing is provided as a file entitled SEQLISTING_ GENOM.143WO.TXT, created Apr. 20, 2016, which is 36 Kb in size. The information in the electronic format of the Sequence Listing is incorporated herein by reference in its entirety.

BACKGROUND

Field

The present disclosure relates to methods and compositions for the detection of vaginal disorders, for example vulvovaginal candidiasis (VVC), trichomoniasis, and bacterial vaginosis (BV). More specifically, the present disclosure relates to the detection of VVC-associated *Candida* species, *Trichomonas vaginalis* (*T. vaginalis*) and a plurality of BV-related bacteria in biological examples, such as vaginal swab samples from women with clinical symptoms of vaginitis and/or vaginosis, by nucleic acid-based test methods.

Description of the Related Art

*Candida* is a genus of yeast and is the most common cause of fungal infections worldwide. Many *Candida* species are found as a harmless commensal, part of a normal flora of a host and can be endosymbionts of hosts including humans. However, in the case of an imbalance or an immunocompromisation of a host, *Candida* is known to invade and cause disease. Some *Candida* species, such as *C. albicans, C. dubliniensis, C. tropicalis, C. parapsilosis, C. krusei*, and *C. glabrata*, are known to be associated with vulvovaginal candidiasis (VVC). *Trichomonas vaginalis* is an anaerobic, flagellated protozoan parasite, which is the causative agent of trichomoniasis. Bacterial vaginosis (BV) is an infection of vagina caused by alteration in normal balance of bacteria in the vagina.

To date, standard tests for diagnosing VVC, trichomoniasis, and BV rely on multiple subjective methods that are interpretive methods. These tests typically involve microscopic examination of wet mount preparation of patient samples (e.g., vaginal discharge), including observation of fungal hyphae or budding yeast for VVC and observation of motile trichomonads for trichomoniasis. The Nugent Score and Amsel's criteria are the most commonly used tests for diagnosing BV. The Nugent Score is a Gram stain scoring system by calculated by assessing for the presence of large Gram-positive rods (*Lactobacillus* morphotypes), small Gram-variable rods (*Gardnerella vaginalis* morphotypes), and curved Gram-variable rods (*Mobiluncus* spp. morphotypes). Amsel's criteria requires at least three of the four following criteria to be present for a confirmed diagnosis: (1) thin, white, yellow, homogeneous discharge, (2) clue cells on microscopy, (3) pH of vaginal fluid >4.5, and (4) release of a fishy odor on adding alkali-10% potassium hydroxide (KOH) solution. These standard tests can be expensive, labor intensive and time consuming, for example, *Candida* needs to be cultured for 48 hours on chromogenic media or up to 7 days on less selective media before a diagnose can be made.

Accordingly, there is a need for developing more efficient and faster methods for detecting vulvovaginal candidiasis, trichomoniasis and bacterial vaginosis, for example a method allowing detecting of the three vaginal disorders in a single assay, in order to effectively deliver proper treatments to patients.

SUMMARY

Disclosed herein are methods and compositions for detecting vulvovaginal candidiasis (VVC), trichomoniasis, and/or bacterial vaginosis (BV).

In one aspect, a method to detect a plurality of BV-related bacteria in a biological sample is disclosed, wherein the plurality of BV-related bacteria comprises *Lactobacillus crispatus, Lactobacillus jensenii, Gardnerella vaginalis, Atopobium vaginae, Megasphaera* Type 1, and BVAB2. In some embodiments, the method comprises:

contacting said biological sample, with a plurality of pairs of primers, wherein the plurality of pairs of primer comprises:

at least one pair of primers capable of hybridizing to the 16S rRNA genes of *Lactobacillus crispatus* and *Lactobacillus jensenii*, wherein each primer in said at least one pair of primers comprises a sequence of SEQ ID NO: 14 or SEQ ID NO: 15, or a sequence that exhibits at least about 85% identity to SEQ ID NO: 14 or SEQ ID NO: 15, at least one pair of primers capable of hybridizing to the 16S rRNA gene of BVAB2, wherein each primer in said at least one pair of primers comprises a sequence of SEQ ID NO: 4 or SEQ ID NO: 5 or a sequence that exhibits at least about 85% identity to SEQ ID NO: 4 or SEQ ID NO: 5, at least one pair of primers capable of hybridizing to the 16S rRNA gene of *Megasphaera* type 1, wherein each primer in said at least one pair of primers comprises a sequence of SEQ ID NO: 7 or SEQ ID NO: 8 or a sequence that exhibits at least about 85% identity to SEQ ID NO: 7 or SEQ ID NO: 8, at least one pair of primers capable of hybridizing to the vly gene of *Gardnerella vaginalis*, wherein each primer in said at least one pair of primers comprises a sequence selected from the group consisting of SEQ ID NOS: 10-12 or a sequence that exhibits at least about 85% identity to a sequence selected from the group consisting of SEQ ID NOS: 10-12, and at least one pair of primers capable of hybridizing to the 16S rRNA gene of *Atopobium vaginae*, wherein each primer in said at least one pair of primers comprises a sequence of SEQ ID NO: 1 or SEQ ID NO: 2, or sequence that exhibits at least about 85% identity to SEQ ID NO: 1 or SEQ ID NO: 2;

generating amplicons of the 16S rRNA sequences of *Atopobium vaginae*, BVAB2, *Megasphaera* type 1, and/or *Lactobacillus crispatus* and *Lactobacillus jensenii*, and/or amplicons of the vly gene sequence of *Gardnerella vaginalis* from said biological sample, if said sample comprises one or more of the BV-related bacteria; and determining the presence or amount of one or more amplified products as an indication of the presence of BV-related bacteria in said biological sample.

In some embodiments, the "contacting" step further comprises contacting said biological sample and said primers with DNA polymerase, a plurality of free nucleotides comprising adenine, thymine, cytosine and guanine, and/or a buffer to produce a reaction mixture. The nucleic acids extracted from the biological sample may comprise or consist of double stranded DNA. A reaction mixture may optionally further contain biovalent cations, monovalent cation potassium ions, one or more detectably labeled probes, and/or any combination thereof.

In some embodiments, the "generating amplicons" step involves (a) heating the reaction mixture to a first predetermined temperature for a first predetermined period of time to separate strands of double stranded DNA present in the biological sample or in the nucleic acids, (b) cooling the reaction mixture to a second predetermined temperature for a second predetermined time under conditions to allow the primers to hybridize with their complementary sequences and to allow the DNA polymerase to extend the primers, and (c) repeating steps (a) and (b) at least 10 to 12 times. In some embodiments, steps (a) and (b) are repeated at least 15, 20, 22 or 25 times.

In some embodiments, the biological sample is a clinical sample. In some embodiments, the biological sample is collected from the urethra, penis, anus, throat, cervix, or vagina. In some embodiments, the biological sample is DNA, RNA or total nucleic acids extracted from a clinical specimen.

In some embodiments, the plurality of pairs of primers comprises a first primer comprising the sequence of SEQ ID NO: 1, a second primer comprising the sequence of SEQ ID NO: 2, a third primer comprising the sequence of SEQ ID NO: 4, a fourth primer comprising the sequence of SEQ ID NO: 5, a fifth primer comprising the sequence of SEQ ID NO: 7, a sixth primer comprising the sequence of SEQ ID NO: 8, a seventh primer comprising the sequence of SEQ ID NO: 10, an eighth primer comprising the sequence of SEQ ID NO: 11, an ninth primer comprising the sequence of SEQ ID NO: 12, a tenth primer comprising the sequence of SEQ ID NO: 14, and an eleventh primer comprising the sequence of SEQ ID NO: 15.

In some embodiments, the pair of primers capable of hybridizing to the 16S rRNA genes of *Lactobacillus crispatus* and *Lactobacillus jensenii* is SEQ ID NOs: 1 and 2; the pair of primers capable of hybridizing to the 16S rRNA gene of BVAB2 is SEQ ID NOs: 4 and 5; the pair of primers capable of hybridizing to the 16S rRNA gene of *Megasphaera* type 1 is SEQ ID NOs: 7 and 8; the pair of primers capable of hybridizing to the vly gene of *Gardnerella vaginalis* is: a) SEQ ID NOs: 10 and 12, or b) SEQ ID NOs: 11 and 12; and the pair of primers capable of hybridizing to the 16S rRNA gene of *Atopobium vaginae* is SEQ ID NOs: 1 and 2.

In some embodiments, the amplification is carried out using a method selected from the group consisting of polymerase chain reaction (PCR), ligase chain reaction (LCR), loop-mediated isothermal amplification (LAMP), strand displacement amplification (SDA), replicase-mediated amplification, Immuno-amplification, nucleic acid sequence based amplification (NASBA), self-sustained sequence replication (3SR), rolling circle amplification, and transcription-mediated amplification (TMA). For example, the PCR can be real-time PCR. In some embodiments, the PCR is quantitative real-time PCR (QRT-PCR). In some embodiments, each primer comprises exogenous nucleotide sequence which allows post-amplification manipulation of amplification products without a significant effect on amplification itself. In some embodiments, each primer is flanked by complementary sequences comprising a fluorophore at the 5' end, and a fluorescence quencher at the 3' end.

In some embodiments, determining the presence or amount of one or more amplified products comprises contacting the amplified products with a plurality of oligonucleotide probes, wherein each of the plurality of oligonucleotide probes comprises a sequence selected from the group consisting of SEQ ID NOs: 3, 6, 9, 13, and 16, or a sequence that exhibits at least about 85% identity to a sequence selected from the group consisting of SEQ ID NOs: 3, 6, 9, 13, and 16. In some embodiments, each of the plurality of oligonucleotide probes comprises, or consists of, a sequence selected from the group consisting of SEQ ID NOs: 3, 6, 9, 13, and 16. In some embodiments, at least one of the plurality of oligonucleotide probes comprises a fluorescence emitter moiety and a fluorescence quencher moiety.

The present disclosure also provides a composition for the detection of a plurality of BV-related bacteria, wherein the plurality of BV-related bacteria comprises *Lactobacillus crispatus*, *Lactobacillus jensenii*, *Gardnerella vaginalis*, *Atopobium vaginae*, *Megasphaera* Type 1, and BVAB2. In some embodiments, the composition comprises:

at least one pair of primers capable of hybridizing to the 16S rRNA genes of *Lactobacillus crispatus* and *Lactobacillus jensenii*, wherein each primer in said at least one pair of primers comprises a sequence of SEQ ID NO: 14 or SEQ ID NO: 15, or a sequence that exhibits at least about 85% identity to SEQ ID NO: 14 or SEQ ID NO: 15, at least one pair of primers capable of hybridizing to the 16S rRNA gene of BVAB2, wherein each primer in said at least one pair of primers comprises a sequence of SEQ ID NO: 4 or SEQ ID NO: 5 or a sequence that exhibits at least about 85% identity to SEQ ID NO: 4 or SEQ ID NO: 5, at least one pair of primers capable of hybridizing to the 16S rRNA gene of *Megasphaera* type 1, wherein each primer in said at least one pair of primers comprises a sequence of SEQ ID NO: 7 or SEQ ID NO: 8 or a sequence that exhibits at least about 85% identity to SEQ ID NO: 7 or SEQ ID NO: 8, at least one pair of primers capable of hybridizing to the vly gene of *Gardnerella vaginalis*, wherein each primer in said at least one pair of primers comprises a sequence selected from the group consisting of SEQ ID NOS: 10-12 or a sequence that exhibits at least about 85% identity to a sequence selected from the group consisting of SEQ ID NOS: 10-12, and at least one pair of primers capable of hybridizing to the 16S rRNA gene of *Atopobium vaginae*, wherein each primer in said at least one pair of primers comprises a sequence of SEQ ID NO: 1 or SEQ ID NO: 2, or sequence that exhibits at least about 85% identity to SEQ ID NO: 1 or SEQ ID NO: 2.

In some embodiments, the at least one pair of primers capable of hybridizing to the 16S rRNA genes of *Lactobacillus crispatus* and *Lactobacillus jensenii* comprises a primer comprising the sequence of SEQ ID NO: 1 and a primer comprising the sequence of SEQ ID NO: 2; the at least one pair of primers capable of hybridizing to the 16S rRNA gene of BVAB2a comprises a primer comprising the sequence of SEQ ID NO: 4 and a primer comprising the sequence of SEQ ID NO: 5; the at least one pair of primers capable of hybridizing to the 16S rRNA gene of *Megasphaera* type 1 comprises a primer comprising the sequence of SEQ ID NO: 7 and a primer comprising the sequence of SEQ ID NO: 8; the at least one pair of primers capable of hybridizing to the vly gene of *Gardnerella vaginalis* comprises a primer comprising the sequence of SEQ ID NO: 10 and a primer comprising the sequence of SEQ ID NO: 11; and the at least one pair of primers capable of hybridizing to the 16S rRNA gene of *Atopobium vaginae* comprises a primer comprising the sequence of SEQ ID NO: 12, a primer comprising the sequence of SEQ ID NO: 14, and a primer comprising the sequence of SEQ ID NO: 15.

The composition can, in some embodiments, further comprises a plurality of oligonucleotide probes, wherein each of the plurality of oligonucleotide probes comprises a sequence selected from the group consisting of SEQ ID NOs: 3, 6, 9, 13, and 16, or a sequence that exhibits at least about 85% identity to a sequence selected from the group consisting of SEQ ID NOs: 3, 6, 9, 13, and 16. In some embodiments, each of the plurality of oligonucleotide probes comprises, or consists of, a sequence selected from the group consisting of SEQ ID NOs: 3, 6, 9, 13, and 16. In some embodiments, at least one of the plurality of probes comprises a fluorescence emitter moiety and a fluorescence quencher moiety.

In another aspect, the present disclosure provides a method to detect vulvovaginal candidiasis (VVC)-associated *Candida* species and *Trichomonas vaginalis* in a biological sample, wherein the VVC-associated *Candida* species comprises *Candida glabrata*, *Candida albicans*, *Candida tropicalis*, *C. dubliniensis*, *C. parapsilosis*, *Candida krusei*. In some embodiments, the method comprises:
contacting said biological sample with a plurality of pairs of primers, wherein the plurality of pairs of primer comprises:
at least one pair of primers capable of hybridizing to the tef1 gene of *Candida glabrata*, wherein each primer in said at least one pair of primers comprises a sequence of SEQ ID NO: 20 or SEQ ID NO: 21 or a sequence that exhibits at least about 85% identity to SEQ ID NO: 20 or SEQ ID NO: 21;
a plurality of primers capable of hybridizing to the tef1 gene of at least one of *Candida albicans, Candida tropicalis, C. dubliniensis*, and *C. parapsilosis*, wherein each primer in said at least one pair of primers comprises a sequence of SEQ ID NO: 23, SEQ ID NO: 24, or SEQ ID NO: 25, or a sequence that exhibits at least about 85% identity to SEQ ID NO: 23, SEQ ID NO: 24, or SEQ ID NO: 25;
at least one pair of primers capable of hybridizing to the tef1 gene of *Candida krusei*, wherein each primer in said at least one pair of primers comprises a sequence of SEQ ID NO: 27 or SEQ ID NO: 28, or sequence that exhibits at least about 85% identity to SEQ ID NO: 27 or SEQ ID NO: 28; and
at least one pair of primers capable of hybridizing to the AP-65 gene of *Trichomonas vaginalis*, wherein each primer in said at least one pair of primers comprises a sequence of SEQ ID NO: 17 or SEQ ID NO: 18, or sequence that exhibits at least about 85% identity to SEQ ID NO: 17 or SEQ ID NO: 18; and
generating amplicons of the tef1 sequences of the *Candida* species and/or amplicons of the AP-65 gene sequence of *Trichomonas vaginalis* from said biological sample, if said sample comprises one or more of the VVC-associated *Candida* species and/or *Trichomonas vaginalis*;
determining the presence or amount of one or more amplified products as an indication of the presence of VVC-associated *Candida* species and *Trichomonas vaginalis* in said biological sample.

In some embodiments, the "contacting" step further comprises contacting said biological sample and said primers with DNA polymerase, a plurality of free nucleotides comprising adenine, thymine, cytosine and guanine, and/or a buffer to produce a reaction mixture. The nucleic acids extracted from the biological sample may comprise or consist of double stranded DNA. A reaction mixture may optionally further contain biovalent cations, monovalent cation potassium ions, one or more detectably labeled probes, and/or any combination thereof.

In some embodiments, the "generating amplicons" step involves (a) heating the reaction mixture to a first predetermined temperature for a first predetermined period of time to separate strands of double stranded DNA present in the biological sample or in the nucleic acids, (b) cooling the reaction mixture to a second predetermined temperature for a second predetermined time under conditions to allow the primers to hybridize with their complementary sequences and to allow the DNA polymerase to extend the primers, and (c) repeating steps (a) and (b) at least 10 to 12 times. In some embodiments, steps (a) and (b) are repeated at least 15, 20, 22 or 25 times.

In some embodiments, the biological sample is a clinical sample. In some embodiments, the biological sample is collected from the urethra, penis, anus, throat, cervix, or vagina. In some embodiments, the biological sample is DNA, RNA or total nucleic acids extracted from a clinical specimen.

In some embodiments, the plurality of pairs of primers comprises a first primer comprising the sequence of SEQ ID NO: 20, a second primer comprising the sequence of SEQ ID NO: 21, a third primer comprising the sequence of SEQ ID NO: 23, a fourth primer comprising the sequence of SEQ ID NO: 24, a fifth primer comprising the sequence of SEQ ID NO: 25, a sixth primer comprising the sequence of SEQ ID NO: 27, a seventh primer comprising the sequence of SEQ ID NO: 28, an eighth primer comprising the sequence of SEQ ID NO: 17, and an ninth primer comprising the sequence of SEQ ID NO: 18.

In some embodiments, the pair of primers capable of hybridizing to the tef1 gene of *Candida glabrata* is SEQ ID NOs: 20 and 21; the primers capable of hybridizing to the tef1 gene of at least one of *Candida albicans, Candida tropicalis, C. dubliniensis*, and *C. parapsilosis* are: a) SEQ ID NOs: 23 and 24, b) SEQ ID NOs: 23 and 35, or c) a combination thereof, the pair of primers capable of hybridizing to the tef1 gene of *Candida krusei* consists of SEQ ID NOs: 27 and 28; and the pair of primers capable of hybridizing to the 16S rRNA gene of *Trichomonas vaginalis* is SEQ ID NOs: 17 and 18.

In some embodiments, the amplification is carried out using a method selected from the group consisting of polymerase chain reaction (PCR), ligase chain reaction (LCR), loop-mediated isothermal amplification (LAMP), strand displacement amplification (SDA), replicase-mediated amplification, Immuno-amplification, nucleic acid sequence based amplification (NASBA), self-sustained sequence replication (3SR), rolling circle amplification, and transcription-mediated amplification (TMA). For example, the PCR can be real-time PCR. In some embodiments, the PCR is quantitative real-time PCR (QRT-PCR).

In some embodiments, each primer comprises exogenous nucleotide sequence which allows post-amplification manipulation of amplification products without a significant effect on amplification itself. In some embodiments, each primer is flanked by complementary sequences comprising a fluorophore at the 5' end, and a fluorescence quencher at the 3' end.

In some embodiments, determining the presence or amount of one or more amplified products comprises contacting the amplified products with a plurality of oligonucleotide probes, wherein each of the plurality of oligonucleotide probes comprises a sequence selected from the group consisting of SEQ ID NOs: 3, 6, 9, 13, and 16, or a sequence that exhibits at least about 85% identity to a sequence selected from the group consisting of SEQ ID NOs: 3, 6, 9, 13, and 16. In some embodiments, each of the plurality of oligonucleotide probes comprises, or consists of, a sequence selected from the group consisting of SEQ ID NOs: 3, 6, 9, 13, and 16.

In some embodiments, at least one of the plurality of oligonucleotide probes comprises a fluorescence emitter moiety and a fluorescence quencher moiety.

Also disclosed herein is a composition for the detection of vulvovaginal candidiasis (VVC)-associated *Candida* species and *Trichomonas vaginalis* in a biological sample, wherein the VVC-associated *Candida* species comprises *Candida glabrata, Candida albicans, Candida tropicalis, C. dubliniensis, C. parapsilosis, Candida krusei*. In some embodiments, the composition comprises:

at least one pair of primers capable of hybridizing to the tef1 gene of *Candida glabrata*, wherein each primer in said at least one pair of primers comprises a sequence of SEQ ID NO: 20 or SEQ ID NO: 21 or a sequence that exhibits at least about 85% identity to SEQ ID NO: 20 or SEQ ID NO: 21;

a plurality of primers capable of hybridizing to the tef1 gene of at least one of *Candida albicans, Candida tropicalis, C. dubliniensis,* and *C. parapsilosis*, wherein each primer in said at least one pair of primers comprises a sequence of SEQ ID NO: 23, SEQ ID NO: 24, or SEQ ID NO: 25, or a sequence that exhibits at least about 85% identity to SEQ ID NO: 23, SEQ ID NO: 24, or SEQ ID NO: 25;

at least one pair of primers capable of hybridizing to the tef1 gene of *Candida krusei*, wherein each primer in said at least one pair of primers comprises a sequence of SEQ ID NO: 27 or SEQ ID NO: 28, or sequence that exhibits at least about 85% identity to SEQ ID NO: 27 or SEQ ID NO: 28; and at least one pair of primers capable of hybridizing to the AP-65 gene of *Trichomonas vaginalis*, wherein each primer in said at least one pair of primers comprises a sequence of SEQ ID NO: 17 or SEQ ID NO: 18, or sequence that exhibits at least about 85% identity to SEQ ID NO: 17 or SEQ ID NO: 18.

In some embodiments, the at least one pair of primers capable of hybridizing to the tef1 gene of *Candida glabrata* comprises a primer comprising the sequence of SEQ ID NO: 20 and a primer comprising the sequence of SEQ ID NO: 21; the plurality of primers capable of hybridizing to the tef1 gene of at least one of *Candida albicans, Candida tropicalis, C. dubliniensis,* and *C. parapsilosis* comprises a primer comprising the sequence of SEQ ID NO: 23, a primer comprising the sequence of SEQ ID NO: 24, and a primer comprising the sequence of SEQ ID NO: 25; the at least one pair of primers capable of hybridizing to the tef1 gene of *Candida krusei* comprises a primer comprising the sequence of SEQ ID NO: 27 and a primer comprising the sequence of SEQ ID NO: 28; and the at least one pair of primers capable of hybridizing to the AP-65 gene of *Trichomonas vaginalis* comprises a primer comprising the sequence of SEQ ID NO: 17 and a primer comprising the sequence of SEQ ID NO: 18.

In some embodiments, the composition can further comprises a plurality of oligonucleotide probes, wherein each of the plurality of oligonucleotide probes comprises a sequence selected from the group consisting of SEQ ID NOs: 22, 26, 29, and 19, or a sequence that exhibits at least about 85% identity to a sequence selected from the group consisting of SEQ ID NOs: 22, 26, 29, and 19. In some embodiments, each of the plurality of oligonucleotide probes comprises, or consists of a sequence selected from the group consisting of SEQ ID NOs: 22, 26, 29, and 19. In some embodiments, at least one of the plurality of probes comprises a fluorescence emitter moiety and a fluorescence quencher moiety.

In one aspect, the present disclosure provides oligonucleotide probes or primers up to about 100 nucleotides in length which are capable of hybridizing to vaginolysin gene (vly) of *Gardnerella vaginalis*, wherein said probe or primer comprises a sequence selected from the group consisting of SEQ ID NOs: 10-13, or sequence that exhibits at least about 85% identity to a sequence selected from the group consisting of SEQ ID NOs: 10-13. In some embodiments, the probe or primer consists of a sequence selected from the group consisting of SEQ ID NOs: 10-13, or sequence that exhibits at least about 85% identity to a sequence selected from the group consisting of SEQ ID NOs: 10-13. In some embodiments, the probe or primer comprises a sequence selected from the group consisting of SEQ ID NOs: 10-13. In some embodiments, the probe or primer consists of a sequence selected from the group consisting of SEQ ID NOs: 10-13.

DETAILED DESCRIPTION

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Provided herein are methods and compositions for the detection of vulvovaginal candidiasis (VVC), trichomoniasis, and bacterial vaginosis (BV). For example, primers and probes that can bind to specific genes of *Candida* species associated with VVC, *Trichomonas vaginalis* (*T. vaginalis*) and BV-related bacteria are provided to determine the presence or absence of the VVC-associated *Candida* species, *T. vaginalis* and BV-related bacteria in a sample, such as a biological sample. In some embodiments, multiplex nucleic acid amplification can be performed to allow the detection of VVC-associated *Candida* species, *T. vaginalis* and BV-related bacteria in a single assay.

Definitions

As used herein, a "nucleic acid" refers to a polymeric compound comprising nucleosides or nucleoside analogs which have nitrogenous heterocyclic bases, or base analogs, linked together by nucleic acid backbone linkages (e.g., phosphodiester bonds) to form a polynucleotide. Non-limiting examples of nucleic acid include RNA, DNA, and analogs thereof. The nucleic acid backbone can include a variety of linkages, for example, one or more of sugar-phosphodiester linkages, peptide-nucleic acid bonds, phosphorothioate or methylphosphonate linkages or mixtures of such linkages in a single oligonucleotide. Sugar moieties in the nucleic acid can be either ribose or deoxyribose, or similar compounds with known substitutions. Conventional nitrogenous bases (e.g., A, G, C, T, U), known base analogs (e.g., inosine), derivatives of purine or pyrimidine bases and "abasic" residues (i.e., no nitrogenous base for one or more backbone positions) are included in the term nucleic acid. That is, a nucleic acid can include only conventional sugars, bases and linkages found in RNA and DNA, or include both conventional components and substitutions (e.g., conventional bases and analogs linked via a methoxy backbone, or conventional bases and one or more base analogs linked via an RNA or DNA backbone).

As used herein, the term "isolate nucleic acids" refers to the purification of nucleic acids from one or more cellular components. One of skill in the art will appreciate that samples processed to "isolate nucleic acids" therefrom can include components and impurities other than nucleic acids. Samples that comprise isolated nucleic acids can be prepared from specimens using any acceptable method known in the art. For example, cells can be lysed using known lysis agents, and nucleic acids can be purified or partially purified from other cellular components. Suitable reagents and protocols for DNA and RNA extractions can be found in, for example, U.S. Patent Application Publication Nos. US 2010-0009351, and US 2009-0131650, respectively (each of which is incorporated herein by reference in its entirety). In nucleic acid testing (e.g., amplification and hybridization methods discussed in further detail below), the extracted nucleic acid solution can be added directly to a reagents (e.g., either in liquid, bound to a substrate, in lyophilized form, or the like, as discussed in further detail below), required to perform a test according to the embodiments disclosed herein.

As used herein, "template" refers to all or part of a polynucleotide containing at least one target nucleotide sequence.

As used herein, a "primer" refers to a polynucleotide that can serve to initiate a nucleic acid chain extension reaction. The length of a primer can vary, for example, from about 5 to about 100 nucleotides, from about 10 to about 50 nucleotides, from about 15 to about 40 nucleotides, or from about 20 to about 30 nucleotides. The length of a primer can be about 10 nucleotides, about 20 nucleotides, about 25 nucleotides, about 30 nucleotides, about 35 nucleotides, about 40 nucleotides, about 50 nucleotides, about 75 nucleotides, about 100 nucleotides, or a range between any two of these values. In some embodiments, the primer has a length of 10 to about 50 nucleotides, i.e., 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, 41, 42, 43, 44, 45, 46, 47, 48, 49, 50, or more nucleotides. In some embodiments, the primer has a length of 18 to 32 nucleotides.

As used herein, a "probe" refers to an polynucleotide that can hybridizes (e.g., specifically) to a target sequence in a nucleic acid, under conditions that allow hybridization, thereby allowing detection of the target sequence or amplified nucleic acid. A probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe. Sequences are "sufficiently complementary" if they allow stable hybridization in appropriate hybridization conditions of a probe oligomer to a target sequence that is not completely complementary to the probe's target-specific sequence. The length of a probe can vary, for example, from about 5 to about 100 nucleotides, from about 10 to about 50 nucleotides, from about 15 to about 40 nucleotides, or from about 20 to about 30 nucleotides. The length of a probe can be about 10 nucleotides, about 20 nucleotides, about 25 nucleotides, about 30 nucleotides, about 35 nucleotides, about 40 nucleotides, about 50 nucleotides, about 100 nucleotides, or a range between any two of these values. In some embodiments, the probe has a length of 10 to about 50 nucleotides. For example, the primers and or probes can be at least 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, 41, 42, 43, 44, 45, 46, 47, 48, 49, 50, or more nucleotides. In some embodiments, the probe can be non-sequence specific.

Preferably, the primers and/or probes can be between 8 and 45 nucleotides in length. For example, the primers and or probes can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. The primer and probe can be modified to contain additional nucleotides at the 5' or the 3' terminus, or both. One of skill in the art will appreciate that additional bases to the 3' terminus of amplification primers (not necessarily probes) are generally complementary to the template sequence. The primer and probe sequences can also be modified to remove nucleotides at the 5' or the 3' terminus. One of skill in the art will appreciate that in order to function for amplification, the primers or probes will be of a minimum length and annealing temperature as disclosed herein.

Primers and probes can bind to their targets at an annealing temperature, which is a temperature less than the melting temperature ($T_m$). As used herein, "$T_m$" and "melting temperature" are interchangeable terms which refer to the temperature at which 50% of a population of double-stranded polynucleotide molecules becomes dissociated into single strands. The formulae for calculating the $T_m$ of polynucleotides are well known in the art. For example, the $T_m$ may be calculated by the following equation: $T_m = 69.3 + 0.41 \times (G+C)\% - 6 - 50/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)×

4° C.]. See, e.g., C. R. Newton et al. PCR, 2nd ed., Springer-Verlag (New York: 1997), p. 24 (incorporated by reference in its entirety, herein). Other more sophisticated computations exist in the art, which take structural as well as sequence characteristics into account for the calculation of $T_m$. The melting temperature of an oligonucleotide can depend on complementarity between the oligonucleotide primer or probe and the binding sequence, and on salt conditions. In some embodiments, an oligonucleotide primer or probe provided herein has a $T_m$ of less than about 90° C. in 50 mM KCl, 10 mM Tris-HCl buffer, for example about 89° C., 88, 87, 86, 85, 84, 83, 82, 81, 80 79, 78, 77, 76, 75, 74, 73, 72, 71, 70, 69, 68, 67, 66, 65, 64, 63, 62, 61, 60, 59, 58, 57, 56, 55, 54, 53, 52, 50, 49, 48, 47, 46, 45, 44, 43, 42, 41, 40, 39° C., or less, including ranges between any two of the listed values.

In some embodiments, the primers disclosed herein, e.g., amplification primers, can be provided as an amplification primer pair, e.g., comprising a forward primer and a reverse primer (first amplification primer and second amplification primer). Preferably, the forward and reverse primers have $T_m$'s that do not differ by more than 10° C., e.g., that differ by less than 10° C., less than 9° C., less than 8° C., less than 7° C., less than 6° C., less than 5° C., less than 4° C., less than 3° C., less than 2° C., or less than 1° C.

The primer and probe sequences may be modified by having nucleotide substitutions (relative to the target sequence) within the oligonucleotide sequence, provided that the oligonucleotide contains enough complementarity to hybridize specifically to the target nucleic acid sequence. In this manner, at least 1, 2, 3, 4, or up to about 5 nucleotides can be substituted. As used herein, the term "complementary" refers to sequence complementarity between regions of two polynucleotide strands or between two regions of the same polynucleotide strand. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Fully complementary" refers to a first polynucleotide that is 100% or "fully" complementary to a second polynucleotide and thus forms a base pair at every nucleotide position. "Partially complementary" also refers to a first polynucleotide that is not 100% complementary (e.g., 90%, or 80% or 70% complementary) and contains mismatched nucleotides at one or more nucleotide positions. In some embodiments, an oligonucleotide includes a universal base.

As used herein, an "exogenous nucleotide sequence" refers to a sequence introduced by primers or probes used for amplification, such that amplification products will contain exogenous nucleotide sequence and target nucleotide sequence in an arrangement not found in the original template from which the target nucleotide sequence was copied.

As used herein, "sequence identity" or "percent identical" as applied to nucleic acid molecules is the percentage of nucleic acid residues in a candidate nucleic acid molecule sequence that are identical with a subject nucleic acid molecule sequence, after aligning the sequences to achieve the maximum percent identity, and not considering any nucleic acid residue substitutions as part of the sequence identity. Nucleic acid sequence identity can be determined using any method known in the art, for example CLUST-ALW, T-COFFEE, BLASTN.

As used herein, the term "sufficiently complementary" refers to a contiguous nucleic acid base sequence that is capable of hybridizing to another base sequence by hydrogen bonding between a series of complementary bases. Complementary base sequences can be complementary at each position in the oligomer sequence by using standard base pairing (e.g., G:C, A:T or A:U) or can contain one or more residues that are not complementary (including abasic positions), but in which the entire complementary base sequence is capable of specifically hybridizing with another base sequence in appropriate hybridization conditions. Contiguous bases can be at least about 80%, at least about 85%, at least about 90%, at least about 95%, at least about 99%, or 100% complementary to a sequence to which an oligomer is intended to hybridize. Substantially complementary sequences can refer to sequences ranging in percent identity from 100, 99, 98, 97, 96, 95, 94, 93, 92, 91, 90, 89, 88, 87, 86, 85, 84, 83, 82, 81, 80, 75, 70 or less, or any number in between, compared to the reference sequence. A skilled artisan can readily choose appropriate hybridization conditions which can be predicted based on base sequence composition, or be determined by using routine testing (see e.g., Green and Sambrook, Molecular Cloning, A Laboratory Manual, 4th ed. (Cold Spring Harbor Laboratory Press, Cold Spring Harbor, N.Y., 2012)).

As used herein, the term "multiplex PCR" refers to a type of PCR where more than one set of primers is included in a reaction allowing one single target, or two or more different targets to be amplified in a single reaction tube. The multiplex PCR can be, for example, a real-time PCR.

Oligonucleotides and Compositions Containing Thereof

As described herein, nucleic acid amplifications can be performed to determine the presence, absence and/or level of *Candida* species, *T. vaginalis*, and/or BV-related bacteria in a sample. Some *Candida* species are known to be associated with VVC, including but not limited to *C. albicans*, *C. dubliniensis*, *C. tropicalis*, *C. parapsilosis*, *C. krusei*, and *C. glabrata*. Many bacteria are also known to be related to BV, including but not limited to, *Lactobacillus* spp. (for example *Lactobacillus crispatus* (*L. crispatus*) and *Lactobacillus jensenii* (*L. jensenii*)), *Gardnerella vaginalis* (*G. vaginalis*), *Atopobium vaginae*, *Megasphaera* Type 1 (*Megasphaera*-1), and BVAB-2. In some embodiments, the presence, absence and/or level of VVC-associated *Candida* species, *T. vaginalis*, and BV-related bacteria is determined by detecting one or more target genes of each of the target organisms using methods known in the art, such as DNA amplifications. In some embodiments, a multiplex PCR can be performed to detect the presence, absence or level for each of the target *Candida* species, *T. vaginalis*, and/or BV-related bacteria. In some embodiments, a multiplex PCR is performed to detect the presence, absence and/or level for each of target VVC-associated *Candida* species, *T. vaginalis*, *L. crispatus*, *L. jensenii*, *G. vaginalis*, *Atopobium vaginae*, *Megasphaera* Type 1, and BVAB-2. In some embodiments, the VVC-associated *Candida* species are *C. albicans*, *C. dubliniensis*, *C. tropicalis*, *C. parapsilosis*, *C. krusei*, and *C. glabrata*.

Each of the target VVC-associated *Candida* species, *T. vaginalis*, and BV-related bacteria can be detected using separate channels in DNA amplifications. In some cases, it can be desirable to use a single fluorescence channel for detecting the presence, absence, and/or level of two or more of the VVC-associated *Candida* species, *T. vaginalis*, and BV-related bacteria. For example, a single fluorescence channel can be used to detect the presence, absence, and/or level of two BV-related bacteria (e.g., BVAB-2 and *Megasphaera*-1). Such combination may, in some embodiments, reduce the amount of reagent needed to conduct the experiment as well as provide an accurate qualitative metric upon which a BV determination can be assessed. Without being bound any particular theory, it is believed that the use of combined markers may increase the sensitivity and specificity of the assay. In some embodiments, separate fluorescence channels are used to detect the presence, absence and/or level of each of *Lactobacillus* spp. (for example *L. crispatus* and *L. jensenii*), *G. vaginalis*, and *Atopobium vaginae*, and a single fluorescence channel is used to detect the presence, absence, and/or level of BVAB-2 and *Megasphaera*-1.

Oligonucleotides (for example amplification primers and probes) that are capable of specifically hybridizing (e.g., under standard nucleic acid amplification conditions, e.g., standard PCR conditions, and/or stringent hybridization conditions) to a target gene region, or complement thereof, in VVC-associated *Candida* species, *T. vaginalis*, *L. crispatus*, *L. jensenii*, *G. vaginalis*, *Atopobium vaginae*, *Megasphaera* Type 1 (*Megasphaera*-1), and BVAB-2 are provided. Amplification of the target gene region of an organism in a sample (e.g., a vaginal swab sample) can, in some embodiments, be indicative of the presence, absence, and/or level of the organism in the sample.

The target gene region can vary. In some embodiments, oligonucleotides (e.g., amplification primers and probes) that are capable of specifically hybridizing (e.g., under standard nucleic acid amplification conditions, e.g., standard PCR conditions, and/or stringent hybridization conditions) to a gene region encoding 16S ribosomal RNA (16S rRNA) in an organism is provided. In some embodiments, the organism is *Atopobium vaginae*. In some embodiments, the organism is BVAB2. In some embodiments, the organism is *Megasphaera* type 1. In some embodiments, the organism is *L. crispatus*. In some embodiments, the microorganism is *L. jensenii*. In some embodiments, 16S rRNA gene is used as the target gene for the DNA amplification to detect the presence, absence and/or level of *Atopobium vaginae*, BVAB-2, *Megasphaera* type 1, *L. crispatus*, and/or *L. jensenii* in the sample. Examples of oligonucleotides capable of specifically hybridizing to the 16S rRNA gene region in BVAB-2 include, but are not limited, SEQ ID NOs: 4-6 as provided in Table 1 and sequences that exhibits at least about 85% identity to a sequence selected from the group consisting of SEQ ID NOs: 4-6. Examples of oligonucleotides capable of specifically hybridizing to the 16S rRNA gene region in *Megasphaera* type 1 include, but are not limited, SEQ ID NOs: 7-9 as provided in Table 1 and sequences that exhibits at least about 85% identity to a sequence selected from the group consisting of SEQ ID NOs: 7-9. In some embodiments, primers and probes that can specifically bind to the 16S rRNA gene region of *Atopobium vaginae* are used in detection of the presence, absence and/or level of *Atopobium vaginae* in a biological sample. Examples of oligonucleotides capable of specifically hybridizing to the 16S rRNA gene region in *Atopobium vaginae* include, but are not limited, SEQ ID NOs: 1-3 as provided in Table 1 and sequences that exhibits at least about 85% identity to a sequence selected from the group consisting of SEQ ID NOs: 1-3. Examples of oligonucleotides capable of specifically hybridizing to the 16S rRNA gene region in *L. crispatus* and *L. jensenii* include, but are not limited, SEQ ID NOs: 14-16 as provided in Table 1 and sequences that exhibits at least about 85% identity to a sequence selected from the group consisting of SEQ ID NOs: 14-16.

Toxin vaginolysin (VLY) is the main virulence factor of *G. vaginalis*, encoded by the gene vly. VLY belongs to the cholesterol dependent cytolysins, a family of pore forming toxins, and is known to disrupt plasma membranes causing cell lysis and are thought to play a key role in the virulence of *G. vaginalis*. In some embodiments, oligonucleotides (e.g., amplification primers and probes) that are capable of specifically hybridizing (e.g., under standard nucleic acid amplification conditions, e.g., standard PCR conditions, and/or stringent hybridization conditions) to a gene region encoding vly in *G. vaginalis* are provided. In some embodiments, vaginolysin (vly) gene is used as the target gene for the DNA amplification to detect the presence, absence and/or level of *G. vaginalis* in the sample. In some embodiments, primers and probes that can specifically bind to the vly gene region of *G. vaginalis* are used in detection of the presence, absence and/or level of *G. vaginalis* in a biological sample. Examples of oligonucleotides capable of specifically hybridizing to the vly gene region in *G. vaginalis* include, but are not limited, SEQ ID NOs: 10-13 as provided in Table 1 and sequences that exhibits at least about 85% identity to a sequence selected from the group consisting of SEQ ID NOs: 10-13.

Protein AP65 is a 65 KDa protein by the parasitic organism *T. vaginalis*, which upon iron repletion acts as a surface adhesin that mediates cytoadherence of the parasite to vaginal epithelial cells. In some embodiments disclosed herein, oligonucleotides (e.g., amplification primers and probes) that are capable of specifically hybridizing (e.g., under standard nucleic acid amplification conditions, e.g., standard PCR conditions, and/or stringent hybridization conditions) to a gene region encoding AP65 in *T. vaginalis* are provided. In some embodiments, AP65 gene is used as the target gene for the DNA amplification to detect the presence, absence and/or level of *T. vaginalis* in the sample. Examples of oligonucleotides capable of specifically hybridizing to the AP65 gene region in *T. vaginalis* include, but are not limited, SEQ ID NOs: 17-19 as provided in Table 1 and sequences that exhibits at least about 85% identity to a sequence selected from the group consisting of SEQ ID NOs: 17-19.

The elongation factor 1 alpha (tef1) gene found in *Candida* species encodes for protein synthesis factor EF, which is involved in the translational process during protein synthesis. As known in the art, tef1 gene is often referred to as tef1 gene or tuf gene as well. In some embodiments disclosed herein, oligonucleotides (e.g., amplification primers and probes) that are capable of specifically hybridizing (e.g., under standard nucleic acid amplification conditions, e.g., standard PCR conditions, and/or stringent hybridization conditions) to a gene region encoding tef in *Candida* species are provided. In some embodiments, tef1 gene is used as the target gene for the DNA amplification to detect the presence, absence and/or level of VVC-associated *Candida* species in the sample. In some embodiments, the VVC-associated *Candida* species comprises *C. albicans, C. dubliniensis, C. tropicalis, C. parapsilosis, C. krusei*, and *C. glabrata*. In some embodiments, the VVC-associated *Candida* species is *Candida krusei*. In some embodiments, the VVC-associated *Candida* species is *Candida glabrata*. In some embodiments, the VVC-associated *Candida* species is *C. albicans, C. dubliniensis, C. tropicalis, C. parapsilosis*, or a combination thereof. Examples of oligonucleotides capable of specifically hybridizing to the tef1 gene region in *C. glabrata* include, but are not limited, SEQ ID NOs: 20-22 as provided in Table 1 and sequences that exhibits at least about 85% identity to a sequence selected from the group consisting of SEQ ID NOs: 20-22. Examples of oligonucleotides capable of specifically hybridizing to the tef1 gene region in *C. albicans, C. dubliniensis, C. tropicalis*, and *C. parapsilosis* include, but are not limited, SEQ ID NOs: 23-26 as provided in Table 1 and sequences that exhibits at least about 85% identity to a sequence selected from the group consisting of SEQ ID NOs: 23-26. Examples of oligonucleotides capable of specifically hybridizing to the tef1 gene region in *C. krusei* include, but are not limited, SEQ ID NOs: 27-29 as provided in Table 1 and sequences that exhibits at least about 85% identity to a sequence selected from the group consisting of SEQ ID NOs: 27-29.

TABLE 1

Primer and probes for detection of VVC-associated
Candida species, T. vaginalis and BV-related species

| Target Organism | Targeted gene | Primer/Probe Name | Primer/Probe Sequences (5'-3') |
|---|---|---|---|
| Atopobium vaginae | 16S rRNA | MenAv248fw | CCCTATCCGCTCCTGATACC (SEQ ID NO: 1) |
| | 16S rRNA | MenAv334rv | CCAAATATCTGCGCATTTCA (SEQ ID NO: 2) |
| | 16S rRNA | MCF-Av-T4 | TCCCCTACCAGACTCAAGCCTGC (SEQ ID NO: 3) (5' fluorophore: FAM, 3' fluorophore: BHQ1) |
| BVAB2 | 16S rRNA | 585F_BVAB2 | GCGGCTAGATAAGTGTGATGTTT (SEQ ID NO: 4) |
| | 16S rRNA | 666R_BVAB2 | CTCTCCAGCACTCAAGCTAAA (SEQ ID NO: 5) |
| | 16S rRNA | BVAB2_613_641 | CAAGGCTTAACCTTGGGGTTCATTACAA (SEQ ID NO: 6) (5' fluorophore: CFO, 3' fluorophore: BHQ1) |
| Megasphaera type 1 | 16S rRNA | 456F_MegaE | GATGCCAACAGTATCCGTCCG (SEQ ID NO: 7) |
| | 16S rRNA | 667R_MegaE | CCTCTCCGACACTCAAGTTCGA (SEQ ID NO: 8) |
| | 16S rRNA | Mega485-506-T | TACCGTAAGAGAAAGCCACGG (SEQ ID NO: 9) (5' fluorophore: CFO, 3' fluorophore: BHQ1) |
| Gardnerella vaginalis | vly | GVvlyfw2 | GCCAACGATGATCGCGTAT (SEQ ID NO: 10) |
| | vly | GVvlyfw2amod | GCCAATAATGACCGCGTAT (SEQ ID NO: 11) |
| | vly | GVvlyrv1 | AGCCGTTCACTGCGGAAGT (SEQ ID NO: 12) |
| | vly | MCF-Gv-T3 | ACAGCACTTTCGCCGCC (SEQ ID NO: 13) (5' fluorophore: Quasar670, 3' fluorophore: BHQ2) |
| Lactobacillus crispatus and Lactobacillus jensenii | 16S rRNA | MCF-Lj_Lc-F8 | TTAAAAGGCGGCGTAAGC (SEQ ID NO: 14) |
| | 16S rRNA | MCF-Lsp-R6 | GCCAGTTACTACCTCTATC (SEQ ID NO: 15) |
| | 16S rRNA | MCF-Lsp-T11 | AAGTCTGATGGAGCAACGCC (SEQ ID NO: 16) (5' fluorophore: ROX, 3' fluorophore: BHQ2) |
| Trichomonas vaginalis | AP-65 | TV.MAX.FP1 | GAAGATTCTGGCAAGATCAAGGA (SEQ ID NO: 17) |
| | AP-65 | TV.MAX.RP1 | ACGACAATGCAGCGGATGT (SEQ ID NO: 18) |
| | AP-65 | TV.MAX.D1-T | ATCCTCCGCAACTACCCACGCCA (SEQ ID NO: 19) (5' fluorophore: FAM, 3' fluorophore: BHQ1) |
| Candida glabrata | tef1 | SiT-Cgla-F8 | CGAACAATTGACTGAAGGTTTG (SEQ ID NO: 20) |
| | tef1 | RT-Cgla-R7 | CGGACTTCAAGAACTTTGGAGA (SEQ ID NO: 21) |
| | tef1 | RT-Cgla-T7 | CTTGTAAGTTCGAAGAATTGTTGGA (SEQ ID NO: 22) (5' fluorophore: CFO, 3' fluorophore: BHQ1) |
| Candida genus* | tef1 | RT-Ca-Cd-Ct-F1 | CCACCAAAGGGTTGTGAC (SEQ ID NO: 23) |
| | tef1 | RT-Ca-Ct-R3 | CAGCATCACCGGATTTGAC (SEQ ID NO: 24) |
| | tef1 | RT-Cpar-R6 | CGGACTTGATGAATTTTGGTTCA (SEQ ID NO: 25) |
| | tef1 | RT-Ca-Cd-T3 | TGCTTGTAAATTCGACACTTTGGTTG (SEQ ID NO: 26) (5' fluorophore: ROX, 3' fluorophore: BHQ2) |
| Candida krusei | tef1 | RT-Ckru-F7 | GCAGCTTCCTTCAATGCTCAA (SEQ ID NO: 27) |
| | tef1 | SiT-Ckru-R10a | ATCACCAGACTTGACAG (SEQ ID NO: 28) |
| | tef1 | RT-Ckru-T9 | CATGTAAGTTCGACGAATTAATCGA (SEQ ID NO: 29) (5' fluorophore: Quasar670, 3' fluorophore: BHQ2) |
| Controls | DrosScaff2 | DrosScaff2-LP | GGCATGGAGGTTGTCCCATTTGTG (SEQ ID NO: 30) |
| | DrosScaff2 | DrosScaff2-UP | GGATCTAGCCGTGTGCCCGCT (SEQ ID NO: 31) |
| | DrosScaff2 | Sign-T1 | TTGATGCCTCTTCACATTGCTCCACCTTTCCT (SEQ ID NO: 32) (5' fluorophore: Quasar705, 3' fluorophore: BHQ3) |

* C. albicans, C. dubliniensis, C. tropicalis, or C. parapsilosis

Also provided herein are oligonucleotides (for example amplification primers or probes) containing 1, 2, 3, 4 or more mismatches or universal nucleotides relative to SEQ ID NOs: 1-32 or the complement thereof, including oligonucleotides that are at least 80% identical (for example at least 81%, 82%, 83%, 84%, 85%, 86%, 87%, 88%, 89%, 90%, 91%, 92%, 93%, 94%, 95%, 96%, 97%, 98%, 99% or 100% identical) to SEQ ID NOs: 1-32 or the complement thereof. In some embodiments, the oligonucleotide comprises a sequence selected from SEQ ID NO: 1-32. In some embodiments, the oligonucleotide comprises a sequence that is at least about 85% identical to a sequence selected from SEQ ID NO: 1-32. In some embodiments, the oligonucleotide consists of a sequence selected from SEQ ID NO: 1-32. In some embodiments, the oligonucleotide consists of a sequence that is at least about 85% identical or at least about 95% identical to a sequence selected from SEQ ID NO: 1-32.

The nucleic acids provided herein can be in various forms. For example, in some embodiments, the nucleic acids are dissolved (either alone or in combination with various other nucleic acids) in solution, for example buffer. In some embodiments, nucleic acids are provided, either alone or in combination with other isolated nucleic acids, as a salt. In some embodiments, nucleic acids are provided in a lyophilized form that can be reconstituted. For example, in some embodiments, the isolated nucleic acids disclosed herein can be provided in a lyophilized pellet alone, or in a lyophilized pellet with other isolated nucleic acids. In some embodiments, nucleic acids are provided affixed to a solid substance, such as a bead, a membrane, or the like. In some embodiments, nucleic acids are provided in a host cell, for example a cell line carrying a plasmid, or a cell line carrying a stably integrated sequence.

Also disclosed herein are compositions, reaction mixtures, and kits that comprise the oligonucleotides (e.g., amplification primers and/or probes) that are capable of specifically hybridizing to the sequence of the 16S rRNA gene of *Atopobium vaginae*, BVAB-2, *Megasphaera* type 1, *L. crispatus*, and/or *L. jensenii*, or a complement thereof. In some embodiments, the composition, reaction mixture, and kit comprise one or more pairs of amplification primers capable of specifically hybridizing to the sequence of 16S rRNA sequence, or a complement thereof, of *Atopobium vaginae*. In some embodiments, the primer comprises a sequence of SEQ ID NO: 1 or 2. In some embodiments, the primer comprises a sequence that is at least about 85% identical, at least about 90%, or at least about 95% identical to a sequence of SEQ ID NO: 1 or 2. In some embodiments, the primer consists of a sequence of SEQ ID NO: 1 or 2. In some embodiments, the primer consists of a sequence that is at least about 85% identical, at least about 90% identical, or at least about 95% identical to a sequence of SEQ ID NO: 1 or 2. In some embodiments, the composition, reaction mixture, and kit comprise one or more probes capable of specifically hybridizing to the sequence of 16S rRNA gene, or complement thereof, of *Atopobium vaginae*. In some embodiments, the probe comprises a sequence of SEQ ID NO: 3. In some embodiments, the probe comprises a sequence that is at least about 85% identical, at least about 90% identical, or at least about 95% identical to a sequence of SEQ ID NO: 3. In some embodiments, the probe consists of a sequence of SEQ ID NO: 3. In some embodiments, the probe consists of a sequence that is at least about 85% identical, at least about 90% identical, or at least about 95% identical to a sequence of SEQ ID NO: 3.

In some embodiments, the composition, reaction mixture, and kit comprise one or more pairs of amplification primers capable of specifically hybridizing to the sequence of 16S rRNA sequence, or a complement thereof, of BVAB-2. In some embodiments, the primer comprises a sequence of SEQ ID NO: 4 or 5. In some embodiments, the primer comprises a sequence that is at least about 85% identical, at least about 90%, or at least about 95% identical to a sequence of SEQ ID NO: 4 or 5. In some embodiments, the primer consists of a sequence of SEQ ID NO: 4 or 5. In some embodiments, the primer consists of a sequence that is at least about 85% identical, at least about 90% identical, or at least about 95% identical to a sequence of SEQ ID NO: 4 or 5. In some embodiments, the composition, reaction mixture, and kit comprise one or more probes capable of specifically hybridizing to the sequence of 16S rRNA gene, or complement thereof, of BVAB-2. In some embodiments, the probe comprises a sequence of SEQ ID NO: 6. In some embodiments, the probe comprises a sequence that is at least about 85% identical, at least about 90% identical, or at least about 95% identical to a sequence of SEQ ID NO: 6. In some embodiments, the probe consists of a sequence of SEQ ID NO: 6. In some embodiments, the probe consists of a sequence that is at least about 85% identical, at least about 90% identical, or at least about 95% identical to a sequence of SEQ ID NO: 6.

In some embodiments, the composition, reaction mixture, and kit comprise one or more pairs of amplification primers capable of specifically hybridizing to the sequence of 16S rRNA sequence, or a complement thereof, of *Megasphaera* type 1. In some embodiments, the primer comprises a sequence of SEQ ID NO: 7 or 8. In some embodiments, the primer comprises a sequence that is at least about 85% identical, at least about 90%, or at least about 95% identical to a sequence of SEQ ID NO: 7 or 8. In some embodiments, the primer consists of a sequence of SEQ ID NO: 7 or 8. In some embodiments, the primer consists of a sequence that is at least about 85% identical, at least about 90% identical, or at least about 95% identical to a sequence of SEQ ID NO: 7 or 8. In some embodiments, the composition, reaction mixture, and kit comprise one or more probes capable of specifically hybridizing to the sequence of 16S rRNA gene, or complement thereof, of *Megasphaera* type 1. In some embodiments, the probe comprises a sequence of SEQ ID NO: 9. In some embodiments, the probe comprises a sequence that is at least about 85% identical, at least about 90% identical, or at least about 95% identical to a sequence of SEQ ID NO: 9. In some embodiments, the probe consists of a sequence of SEQ ID NO: 9. In some embodiments, the probe consists of a sequence that is at least about 85% identical, at least about 90% identical, or at least about 95% identical to a sequence of SEQ ID NO: 9.

In some embodiments, the composition, reaction mixture, and kit comprise one or more pairs of amplification primers capable of specifically hybridizing to the sequence of 16S rRNA sequence, or a complement thereof, of *L. crispatus* and/or *L. jensenii*. In some embodiments, the primer comprises a sequence of SEQ ID NO: 14 or 15. In some embodiments, the primer comprises a sequence that is at least about 85% identical, at least about 90%, or at least about 95% identical to a sequence of SEQ ID NO: 14 or 15. In some embodiments, the primer consists of a sequence of SEQ ID NO: 14 or 15. In some embodiments, the primer consists of a sequence that is at least about 85% identical, at least about 90% identical, or at least about 95% identical to a sequence of SEQ ID NO: 14 or 15. In some embodiments, the composition, reaction mixture, and kit comprise one or more probes capable of specifically hybridizing to the sequence of 16S rRNA gene, or complement thereof, of *L. crispatus* and/or *L. jensenii*. In some embodiments, the probe comprises a sequence of SEQ ID NO: 16. In some embodiments, the probe comprises a sequence that is at least about 85% identical, at least about 90% identical, or at least about 95% identical to a sequence of SEQ ID NO: 16. In some embodiments, the probe consists of a sequence of SEQ ID NO: 16. In some embodiments, the probe consists of a sequence that is at least about 85% identical, at least about 90% identical, or at least about 95% identical to a sequence of SEQ ID NO: 16.

Compositions, reaction mixtures, and kits that that comprise the oligonucleotides (e.g., amplification primers and/or probes) that are capable of specifically hybridizing to the sequence of vly gene of *G. vaginalis*, or a complement thereof, are also provided. In some embodiments, the composition, reaction mixture, and kit comprise one or more pairs of amplification primers capable of specifically hybridizing to the sequence of vly gene sequence of *G. vaginalis*, or a complement thereof. In some embodiments, the primer comprises a sequence of SEQ ID NO: 10, 11, or 12. In some embodiments, the primer comprises a sequence that is at least about 85% identical, at least about 90%, or at least about 95% identical to a sequence of SEQ ID NO: 10, 11 or 12. In some embodiments, the primer consists of a sequence of SEQ ID NO: 10, 11 or 12. In some embodiments, the primer consists of a sequence that is at least about 85% identical, at least about 90% identical, or at least about 95% identical to a sequence of SEQ ID NO: 10, 11 or 12. In some embodiments, the composition, reaction mixture, and kit comprise one or more probes capable of specifically hybridizing to the sequence of vly gene of *G. vaginalis*, or complement thereof. In some embodiments, the probe comprises a sequence of SEQ ID NO: 13. In some embodiments, the probe comprises a sequence that is at least about 85% identical, at least about 90% identical, or at least about 95% identical to a sequence of SEQ ID NO: 13. In some embodiments, the probe consists of a sequence of SEQ ID 13. In some embodiments, the probe consists of a sequence that is at least about 85% identical, at least about 90% identical, or at least about 95% identical to a sequence of SEQ ID NO: 13.

Compositions, reaction mixture, and kits that that comprise the oligonucleotides (e.g., amplification primers and/or probes) that are capable of specifically hybridizing to the sequence of the AP-65 gene of *T. vaginalis*, or a complement thereof, are provided. In some embodiments, the composition, reaction mixture, and kit comprise one or more pairs of amplification primers capable of specifically hybridizing to the sequence of the AP-65 gene sequence of *T. vaginalis*, or a complement thereof. In some embodiments, the primer comprises a sequence of SEQ ID NO: 17 or 18. In some embodiments, the primer comprises a sequence that is at least about 85% identical, at least about 90%, or at least about 95% identical to a sequence of SEQ ID NO: 17 or 18. In some embodiments, the primer consists of a sequence of SEQ ID NO: 17 or 18. In some embodiments, the primer consists of a sequence that is at least about 85% identical, at least about 90% identical, or at least about 95% identical to a sequence of SEQ ID NO: 17 or 18. In some embodiments, the composition, reaction mixture, and kit comprise one or more probes capable of specifically hybridizing to the sequence of AP-65 gene of *T. vaginalis*, or complement thereof. In some embodiments, the probe comprises a sequence of SEQ ID NO: 19. In some embodiments, the probe comprises a sequence that is at least about 85% identical, at least about 90% identical, or at least about 95% identical to a sequence of SEQ ID NO: 19. In some embodiments, the probe consists of a sequence of SEQ ID NO: 19. In some embodiments, the probe consists of a sequence that is at least about 85% identical, at least about 90% identical, or at least about 95% identical to a sequence of SEQ ID NO: 19.

Compositions, reaction mixtures, and kits that comprise the oligonucleotides (e.g., amplification primers and/or probes) that are capable of specifically hybridizing to the sequence of tef1 gene of one or more *Candida* species, or complement thereof, are provided. In some embodiments, the composition, reaction mixture, and kit comprise one or more pairs of amplification primers capable of specifically hybridizing to the sequence of tef1 gene sequence of *Candida glabrata*, or complement thereof. In some embodiments, the primer comprises a sequence of SEQ ID NO: 20 or 21. In some embodiments, the primer comprises a sequence that is at least about 85% identical, at least about 90%, or at least about 95% identical to a sequence of SEQ ID NO: 20 or 21. In some embodiments, the primer consists of a sequence of SEQ ID NO: 20 or 21. In some embodiments, the primer consists of a sequence that is at least about 85% identical, at least about 90% identical, or at least about 95% identical to a sequence of SEQ ID NO: 20 or 21. In some embodiments, the composition, reaction mixture, and kit comprise one or more probes capable of specifically hybridizing to the sequence of tef1 gene *Candida glabrata*, or complement thereof. In some embodiments, the probe comprises a sequence of SEQ ID NO: 22, 26 or 29. In some embodiments, the probe comprises a sequence that is at least about 85% identical, at least about 90% identical, or at least about 95% identical to a sequence of SEQ ID NO: 22. In some embodiments, the probe consists of a sequence of SEQ ID NO: 22. In some embodiments, the probe consists of a sequence that is at least about 85% identical, at least about 90% identical, or at least about 95% identical to a sequence of SEQ ID NO: 22.

In some embodiments, the composition, reaction mixture, and kit comprise one or more pairs of amplification primers capable of specifically hybridizing to the sequence of tef1 gene sequence of one or more *Candida* species, or complement thereof, wherein the *Candida* species comprises *C. albicans, C. dubliniensis, C. tropicalis*, and *C. parapsilosis*. In some embodiments, the primer comprises a sequence of SEQ ID NO: 20, 21, 23, 24, 25, 27, or 28. In some embodiments, the primer comprises a sequence that is at least about 85% identical, at least about 90%, or at least about 95% identical to a sequence of SEQ ID NO: 23, 24 or 25. In some embodiments, the primer consists of a sequence of SEQ ID NO: 23, 24 or 25 In some embodiments, the primer consists of a sequence that is at least about 85% identical, at least about 90% identical, or at least about 95% identical to a sequence of SEQ ID NO: 23, 24 or 25. In some embodiments, the composition, reaction mixture, and kit comprise one or more probes capable of specifically hybridizing to the sequence of tef1 gene of one or more *Candida* species, or complement thereof, wherein the *Candida* species comprises *C. albicans, C. dubliniensis, C. tropicalis*, and *C. parapsi*. In some embodiments, the probe comprises a sequence of SEQ ID NO: 26. In some embodiments, the probe comprises a sequence that is at least about 85% identical, at least about 90% identical, or at least about 95% identical to a sequence of SEQ ID NO: 26. In some embodiments, the probe consists of a sequence of SEQ ID NO: 26. In some embodiments, the probe consists of a sequence that is at least about 85% identical, at least about 90% identical, or at least about 95% identical to a sequence of SEQ ID NO: 26.

In some embodiments, the composition, reaction mixture, and kit comprise one or more pairs of amplification primers capable of specifically hybridizing to the sequence of tef1 gene sequence of *Candida krusei*, or complement thereof. In some embodiments, the primer comprises a sequence of SEQ ID NO: 27 or 28. In some embodiments, the primer comprises a sequence that is at least about 85% identical, at least about 90%, or at least about 95% identical to a sequence of SEQ ID NO: 27 or 28. In some embodiments, the primer consists of a sequence of SEQ ID NO: 27 or 28. In some embodiments, the primer consists of a sequence that is at least about 85% identical, at least about 90% identical, or at least about 95% identical to a sequence of SEQ ID NO: 27 or 28. In some embodiments, the composition, reaction mixture, and kit comprise one or more probes capable of specifically hybridizing to the sequence of tef1 gene of *Candida krusei*, or complement thereof. In some embodiments, the probe comprises a sequence of SEQ ID NO: 29. In some embodiments, the probe comprises a sequence that is at least about 85% identical, at least about 90% identical, or at least about 95% identical to a sequence of SEQ ID NO: 29. In some embodiments, the probe consists of a sequence of SEQ ID NO: 29. In some embodiments, the probe consists of a sequence that is at least about 85% identical, at least about 90% identical, or at least about 95% identical to a sequence of SEQ ID NO: 29.

Oligonucleotide probes can, in some embodiments, include a detectable moiety. For example, the oligonucleotide probes disclosed herein can comprise a radioactive label. Non-limiting examples of radioactive labels include $^3$H, $^{14}$C, $^{32}$P, and $^{35}$S. In some embodiments, oligonucleotide probes can include one or more non-radioactive detectable markers or moieties, including but not limited to ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe. For example, oligonucleotide probes labeled with one or more dyes, such that upon hybridization to a template nucleic acid, a detectable change in fluorescence is generated. While non-specific dyes may be desirable for some applications, sequence-specific probes can provide more accurate measurements of amplification. One configuration of sequence-specific probe can include one end of the probe tethered to a fluorophore, and the other end of the probe tethered to a quencher. When the probe is unhybridized, it can maintain a stem-loop configuration, in which the fluorophore is quenched by the quencher, thus preventing the fluorophore from fluorescing. When the probe is hybridized to a template nucleic sequence, it is linearized, distancing the fluorophore from the quencher, and thus permitting the fluorophore to fluoresce. Another configuration of sequence-specific probe can include a first probe tethered to a first fluorophore of a FRET pair, and a second probe tethered to a second fluorophore of a FRET pair. The first probe and second probe can be configured to hybridize to sequences of an amplicon that are within sufficient proximity to permit energy transfer by FRET when the first probe and second probe are hybridized to the same amplicon.

In some embodiments, the sequence specific probe comprises an oligonucleotide as disclosed herein conjugated to a fluorophore. In some embodiments, the probe is conjugated to two or more fluorophores. Examples of fluorophores include: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G)(emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, CAL fluor orange, and the like.

In some embodiments, the probe is conjugated to a quencher. A quencher can absorb electromagnetic radiation and dissipate it as heat, thus remaining dark. Example quenchers include Dabcyl, NFQ's, such as BHQ-1 or BHQ-2 (Biosearch), IOWA BLACK FQ (IDT), and IOWA BLACK RQ (IDT). In some embodiments, the quencher is selected to pair with a fluorophore so as to absorb electromagnetic radiation emitted by the fluorophore. Fluorophore/quencher pairs useful in the compositions and methods disclosed herein are well-known in the art, and can be found, e.g., described in Marras, "Selection of Fluorophore and Quencher Pairs for Fluorescent Nucleic Acid Hybridization Probes" available at www.molecular-beacons.org/download/marras,mmb06%28335%293.pdf.

In some embodiments, a fluorophore is attached to a first end of the probe, and a quencher is attached to a second end of the probe. Attachment can include covalent bonding, and can optionally include at least one linker molecule positioned between the probe and the fluorophore or quencher. In some embodiments, a fluorophore is attached to a 5' end of a probe, and a quencher is attached to a 3' end of a probe. In some embodiments, a fluorophore is attached to a 3' end of a probe, and a quencher is attached to a 5' end of a probe. Examples of probes that can be used in quantitative nucleic acid amplification include molecular beacons, SCORPION™ probes (Sigma), TAQMAN™ probes (Life Technologies) and the like. Other nucleic acid detection technologies that are useful in the embodiments disclosed herein include, but are not limited to nanoparticle probe technology (See, Elghanian, et al. (1997) Science 277:1078-1081.) and Amplifluor probe technology (See, U.S. Pat. Nos. 5,866, 366; 6,090,592; 6,117,635; and 6,117,986).

Some embodiments provide a composition for the detection of a plurality of BV-related bacteria, wherein the composition comprises: primers capable of hybridizing to the 16S rRNA genes of *L. crispatus* and/or *L. jensenii*, wherein each primer comprises a sequence of SEQ ID NO: 14 or SEQ ID NO: 15, or a sequence that exhibits at least about 85% identity to SEQ ID NO: 14 or SEQ ID NO: 15; primers capable of hybridizing to the 16S rRNA gene of BVAB2, wherein each primer comprises a sequence of SEQ ID NO: 4 or SEQ ID NO: 5 or a sequence that exhibits at least about 85% identity to SEQ ID NO: 4 or SEQ ID NO: 5; primers capable of hybridizing to the 16S rRNA gene of *Megasphaera* type 1, wherein each primer comprises a sequence of SEQ ID NO: 7 or SEQ ID NO: 8 or a sequence that exhibits at least about 85% identity to SEQ ID NO: 7 or SEQ ID NO: 8; primers capable of hybridizing to the vly gene of *G. vaginalis*, wherein each primer comprises a sequence selected from the group consisting of SEQ ID NOS: 10-12 or a sequence that exhibits at least about 85% identity to a sequence selected from the group consisting of SEQ ID NOS: 10-12, and primers capable of hybridizing to the 16S rRNA gene of *Atopobium vaginae*, wherein each primer comprises a sequence of SEQ ID NO: 1 or SEQ ID NO: 2, or sequence that exhibits at least about 85% identity to SEQ ID NO: 1 or SEQ ID NO: 2.

In some embodiments, the primers capable of hybridizing to the 16S rRNA genes of *L. crispatus* and/or *L. jensenii* comprise, or consist of, a primer comprising the sequence of SEQ ID NO: 1 and a primer comprising the sequence of SEQ ID NO: 2; the primers capable of hybridizing to the 16S rRNA gene of BVAB2 comprise, or consist of, a primer comprising the sequence of SEQ ID NO: 4 and a primer comprising the sequence of SEQ ID NO: 5; the primers capable of hybridizing to the 16S rRNA gene of *Megasphaera* type 1 comprise, consists of, a primer comprising the sequence of SEQ ID NO: 7 and a primer comprising the sequence of SEQ ID NO: 8; the primers capable of hybridizing to the vly gene of *G. vaginalis* comprise, or consist of, a primer comprising the sequence of SEQ ID NO: 10 and a primer comprising the sequence of SEQ ID NO: 11; and the primers capable of hybridizing to the 16S rRNA gene of *Atopobium vaginae* comprise, or consist of a primer comprising the sequence of SEQ ID NO: 12, a primer comprising the sequence of SEQ ID NO: 14, and a primer comprising the sequence of SEQ ID NO: 15.

The composition can further comprise a plurality of oligonucleotide probes, wherein each of the plurality of oligonucleotide probes comprises a sequence selected from the group consisting of SEQ ID NOs: 3, 6, 9, 13, and 16, or a sequence that exhibits at least about 85% identity to a sequence selected from the group consisting of SEQ ID NOs: 3, 6, 9, 13, and 16. In some embodiments, each of the plurality of oligonucleotide probes comprises, or consists of, a sequence selected from the group consisting of SEQ ID NOs: 3, 6, 9, 13, and 16.

Some embodiments disclosed herein provide a composition for the detection of VVC-associated *Candida* species and *T. vaginalis* in a biological sample, wherein the composition comprises: primers capable of hybridizing to the tef1 gene of *Ca. glabrata*, wherein each primer comprises a sequence of SEQ ID NO: 20 or SEQ ID NO: 21 or a sequence that exhibits at least about 85% identity to SEQ ID NO: 20 or SEQ ID NO: 21; primers capable of hybridizing to the tef1 gene of at least one of *C. albicans, C. tropicalis, C. dubliniensis*, and *C. parapsilosis*, wherein each primer comprises a sequence of SEQ ID NO: 23, SEQ ID NO: 24, or SEQ ID NO: 25, or a sequence that exhibits at least about 85% identity to SEQ ID NO: 23, SEQ ID NO: 24, or SEQ ID NO: 25; primers capable of hybridizing to the tef1 gene of *C. krusei*, wherein each primer comprises a sequence of SEQ ID NO: 27 or SEQ ID NO: 28, or sequence that exhibits at least about 85% identity to SEQ ID NO: 27 or SEQ ID NO: 28; and primers capable of hybridizing to the AP-65 gene of *T. vaginalis*, wherein each primer comprises a sequence of SEQ ID NO: 17 or SEQ ID NO: 18, or sequence that exhibits at least about 85% identity to SEQ ID NO: 17 or SEQ ID NO: 18.

In some embodiments, the primers capable of hybridizing to the tef1 gene of *C. glabrata* comprise, or consist of, a primer comprising the sequence of SEQ ID NO: 20 and a primer comprising the sequence of SEQ ID NO: 21; the primers capable of hybridizing to the tef1 gene of at least one of *C. albicans, C. tropicalis, C. dubliniensis*, and *C. parapsilosis* comprise, or consist of, a primer comprising the sequence of SEQ ID NO: 23, a primer comprising the sequence of SEQ ID NO: 24, and a primer comprising the sequence of SEQ ID NO: 25; the primers capable of hybridizing to the tef1 gene of *C. krusei* comprise, or consist of, a primer comprising the sequence of SEQ ID NO: 27 and a primer comprising the sequence of SEQ ID NO: 28; and the primers capable of hybridizing to the AP-65 gene of *T. vaginalis* comprise, or consist of a primer comprising the sequence of SEQ ID NO: 17 and a primer comprising the sequence of SEQ ID NO: 18.

The composition can, in some embodiments, further comprises a plurality of oligonucleotide probes, wherein each of the plurality of oligonucleotide probes comprises a sequence selected from the group consisting of SEQ ID NOs: 22, 26, 29, and 19, or a sequence that exhibits at least about 85% identity to a sequence selected from the group consisting of SEQ ID NOs: 22, 26, 29, and 19. In some embodiments, each of the plurality of oligonucleotide probes comprises, or consists of, a sequence selected from the group consisting of SEQ ID NOs: 22, 26, 29, and 19.

Any probes described herein can comprise a fluorescence emitter moiety and a fluorescence quencher moiety.

As disclosed herein, a reaction mixture can comprise one or more of the primers disclosed herein, one or more of the probes disclosed herein (e.g., the fluorophore-containing probes), or any combination thereof. In some embodiments, the reaction mixture comprises one or more of the primer and/or probe-containing composition disclosed herein. The reaction mixture can also comprise various additional components. Examples of the additional components in the reaction mixture include, but are not limited to, template DNA, DNA polymerase (e.g., Taq DNA polymerase), deoxynucleotides (dNTPs), buffer solution, biovalent cations, monovalent cation potassium ions, and any combination thereof. In some embodiments, the reaction mixture is a master mix for real-time PCR.

Samples

The methods and compositions disclosed herein are suitable for detecting vaginal disorders, such as VVC, trichomoniasis and BV, in a wide variety of samples. As used herein, a "sample" refers to any type of material of biological origin taken from one or more number of subjects that are suspected of suffering from VVC, trichomoniasis, and/or BV. The sample can comprise, for example, fluid, tissue or cell. The sample can comprise a biological material taken directly from a subject, or cultured call or tissues, or any fraction or products produced from or derived from biological materials. A sample can be purified, partially purified, unpurified, enriched, or amplified.

The sample can be a biological sample, for example a clinical sample. In some embodiments, the sample is taken from a biological source, such as vagina, urethra, penis, anus, throat, cervix, fermentation broths, cell cultures, and the like. The sample can comprise, for example, fluid and cells from vagina. The biological sample can be used (i) directly as obtained from the subject or source, or (ii) following a pre-treatment to modify the character of the sample. Thus, the test sample can be pre-treated prior to use, for example, by disrupting cells or viral particles, preparing liquids from solid materials, diluting viscous fluids, filtering liquids, concentrating liquids, inactivating interfering components, adding reagents, purifying nucleic acids, and the like. Accordingly, a "biological sample" as used herein includes nucleic acids (DNA, RNA or total nucleic acids) extracted from a clinical or biological specimen. Sample preparation can also include using a solution that contains buffers, salts, detergents, and/or the like which are used to prepare the sample for analysis. In some embodiments, the sample is processed before molecular testing. In some embodiments, the sample is analyzed directly, and is not pre-processed prior to testing. The sample can be, for example, a vaginal sample, such as a single vaginal swab sample. In some embodiments, the sample is a vaginal swab sample from a female with clinical symptoms of vaginitis and/or vaginosis.

Vaginal or urine samples are often infected with multiple organisms. The disclosed primers and probes are tolerant to mixed infections of the vaginal or urine matrix.

In some embodiments, a sample to be tested is processed prior to performing the methods disclosed herein. For example, in some embodiments, the sample can be isolated, concentrated, or subjected to various other processing steps prior to performing the methods disclosed herein. For example, in some embodiments, the sample can be processed to isolate nucleic acids from the sample prior to contacting the sample with the oligonucleotides, as disclosed herein. In some embodiments, the methods disclosed herein are performed on the sample without culturing the sample in vitro. In some embodiments, the methods disclosed herein are performed on the sample without isolating nucleic acids from the sample prior to contacting the sample with oligonucleotides as disclosed herein.

Sample Extraction

In typical sample extractions, cells are lysed by mechanical shearing with glass beads as described in U.S. Pat. No. 7,494,771, incorporated by reference in its entirety herein, to lyse the target organisms. As disclosed in WO03/008636, such a generic method of cell lysis is efficient for a wide variety of target organisms and specimen matrices. There are also other less universal lysis methods that are designed specifically to target a certain species or group of organisms, or which exploit specific enzymatic or chemical activities. For example, ACP enzyme is commonly used to lyse of Gram-positive organisms (Ezaki et al., J. Clin. Microbiol., 16(5):844-846 (1982); Paule et al., J. Mol. Diagn., 6(3):191-196 (2004); U.S. Pat. No. 3,649,454; all incorporated by reference in their entirety herein) and mycobacteria (U.S. Pat. No. 5,185,242, incorporated by reference in its entirety) but is generally considered to be less efficacious with respect to lysis of Gram-negative species such as *E. coli* and *Pseudomonas aeruginosa* (U.S. Pat. No. 3,649,454, incorporated by reference in its entirety).

Inventors of the present disclosure was surprised to find that neither ACP nor Proteinase K can efficiently lyse *Candida* cells walls, and lyticase described in patent U.S. Pat. No. 3,716,452 (incorporated by reference in its entirety) can effectively lyse cell walls of *Candida* species. Cell lysis can be performed under various temperatures, for example between 18° C. to 75° C., for example, 37° C. and 50° C. It is advantageous to lyse the cells at 37° C. to achieve higher lysis efficiency as compared to 50° C. (LND490E38). In some embodiments, lyticase is used to lyse *Candida* species, including but not limited to *C. albicans, C. krusei, C. parapsilosis, C. tropicalis,* and *C. glabrata*. The time required to achieve desired lysis efficiency for the sample is not particularly limited. In some embodiments, it requires about 10 minute to achieve desired lysis efficiency of the sample.

Nucleic Acid Testing

The methods described herein can include, for example, nucleic acid testing. For example, the test can include testing for target nucleic acid sequences in a sample. Various forms of nucleic acid testing can be used in the embodiments disclosed herein, including but not limited to, testing that involves nucleic acid amplification.

As used herein, nucleic acid amplification refers to any known procedure for obtaining multiple copies of a target nucleic acid sequence or its complement or fragments thereof, using sequence-specific methods. Examples of known amplification methods include, but are not limited to, polymerase chain reaction (PCR), ligase chain reaction (LCR), loop-mediated isothermal amplification (LAMP), strand displacement amplification (SDA) (e.g., multiple displacement amplification (MDA)), replicase-mediated amplification, immuno-amplification, nucleic acid sequence based amplification (NASBA), self-sustained sequence replication (3SR), rolling circle amplification, and transcription-mediated amplification (TMA). See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Dean et al, "Multiple displacement amplification," U.S. Pat. No. 6,977,148; Notomi et al., "Process for Synthesizing Nucleic Acid," U.S. Pat. No. 6,410,278; Landegren et al. U.S. Pat. No. 4,988,617 "Method of detecting a nucleotide change in nucleic acids"; Birkenmeyer, "Amplification of Target Nucleic Acids Using Gap Filling Ligase Chain Reaction," U.S. Pat. No. 5,427,930; Cashman, "Blocked-Polymerase Polynucleotide Immunoassay Method and Kit," U.S. Pat. No. 5,849,478; Kacian et al., "Nucleic Acid Sequence Amplification Methods," U.S. Pat. No. 5,399,491; Malek et al., "Enhanced Nucleic Acid Amplification Process," U.S. Pat. No. 5,130,238; Lizardi et al., BioTechnology, 6:1197 (1988); Lizardi et al., U.S. Pat. No. 5,854,033 "Rolling circle replication reporter systems." In some embodiments, two or more of the aforementioned nucleic acid amplification methods can be performed, for example sequentially.

For example, LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.).

PCR is a method well-known in the art for amplification of nucleic acids. PCR involves amplification of a target sequence using two or more extendable sequence-specific oligonucleotide primers that flank the target sequence. The nucleic acid containing the target sequence of interest is subjected to a program of multiple rounds of thermal cycling (denaturation, annealing and extension) in the presence of the primers, a thermostable DNA polymerase (e.g., Taq polymerase) and various dNTPs, resulting in amplification of the target sequence. PCR uses multiple rounds of primer extension reactions in which complementary strands of a defined region of a DNA molecule are simultaneously synthesized by a thermostable DNA polymerase. At the end of each cycle, each newly synthesized DNA molecule acts as a template for the next cycle. During repeated rounds of these reactions, the number of newly synthesized DNA strands increases exponentially such that after 20 to 30 reaction cycles, the initial template DNA will have been replicated several thousand-fold or million-fold. Methods for carrying out different types and modes of PCR are thoroughly described in the literature, for example in "PCR Primer: A Laboratory Manual" Dieffenbach and Dveksler, eds. Cold Spring Harbor Laboratory Press, 1995, and by Mullis et al. in patents (e.g., U.S. Pat. Nos. 4,683,195, 4,683,202 and 4,800,159) and scientific publications (e.g. Mullis et al. 1987, Methods in Enzymology, 155:335-350) where the contents of each reference are hereby incorporated by reference in their entireties.

PCR can generate double-stranded amplification products suitable for post-amplification processing. If desired, amplification products can be detected by visualization with agarose gel electrophoresis, by an enzyme immunoassay format using probe-based colorimetric detection, by fluorescence emission technology, or by other detection means known to one of skill in the art.

A wide variety of PCR methods have been described in many sources, for example, Ausubel et al. (eds.), Current Protocols in Molecular Biology, Section 15, John Wiley & Sons, Inc., New York (1994). Examples of PCR method include, but not limited to, Real-Time PCR, End-Point PCR, Amplified fragment length polymorphism PCR (AFLP-PCR), Alu-PCR, Asymmetric PCR, Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR.

Real-time PCR, also called quantitative real time polymerase chain reaction (QRT-PCR), can be used to simultaneously quantify and amplify a specific part of a given nucleic acid molecule. It can be used to determine whether a specific sequence is present in the sample; and if it is present, the number of copies of the sequence that are present. The term "real-time" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with fluorescence resonance energy transfer (FRET) probes measures fluorescent dye signal changes from cycle-to-cycle, preferably minus any internal control signals. The real-time procedure follows the general pattern of PCR, but the nucleic acid is quantified after each round of amplification. Two examples of method of quantification are the use of fluorescent dyes (e.g., SYBRGreen) that intercalate into double-stranded DNA, and modified DNA oligonucleotide probes that fluoresce when hybridized with a complementary DNA. Intercalating agents have a relatively low fluorescence when unbound, and a relatively high fluorescence upon binding to double-stranded nucleic acids. As such, intercalating agents can be used to monitor the accumulation of double strained nucleic acids during a nucleic acid amplification reaction. Examples of such non-specific dyes useful in the embodiments disclosed herein include intercalating agents such as SYBR Green I (Molecular Probes), propidium iodide, ethidium bromide, and the like.

Vaginal samples are often infected with multiple organisms. The disclosed primers and probes are tolerant to mixed infections of the vaginal matrix. Because of the specific target sequences, primers and probes, the methods and compositions disclosed herein can be used to detect the presence/absence or level of VVC-associated *Candida* species, *T. vaginalis*, and/or BV-related bacteria in a sample with high sensitivity, specificity and accuracy.

The primers disclosed herein can be paired with additional PCR systems using a uniform chemistry and thermal PCR profile to provide a panel of assays for the detection of vaginal organisms, to improve overall assay sensitivity and robustness.

In some embodiments, multiplex PCR is performed to amplify and detect, e.g., by direct or indirect means, the presence or absence of VVC-associated *Candida* species, *T. vaginalis*, and BV-related bacteria to allow diagnose of VVC, Trichomoniasis and BV using one test. In the multiplex PCR, the presence or absence of VVC-associated *Candida* species can be determined by amplifying and detecting the presence or absence of tef1 gene of *C. albicans, C. dubliniensis, C. tropicalis, C. parapsilosis, C. krusei*, and *C. glabrata*; the presence or absence of *T. vaginalis* can be determined by amplifying and detecting the presence or absence of AP-65 gene of *T. vaginalis*; the presence or absence of BV-related bacteria, including *L. crispatus, L. jensenii, G. vaginalis, Atopobium vaginae, Megasphaera* Type 1, and BVAB-2, can be determined by amplifying and detecting the presence or absence of 16S rRNA gene of *Atopobium vaginae*, BVAB-2, *Megasphaera* Type 1, and the presence or absence of vly gene of *G. vaginalis*.

Accordingly, some embodiments for the detection and/or identification of VVC-associated *Candida* species, *T. vaginalis*, and BV-related bacteria in a sample include the steps of providing a test sample; and contacting the sample with oligonucleotide primers that can specifically hybridize and amplify (1) tef1 genes of *C. albicans, C. dubliniensis, C. tropicalis, C. parapsilosis, C. krusei*, and *C. glabrata*, (2) AP-65 gene of *T. vaginalis*, (3) 16S rRNA genes of *Atopobium vaginae*, BVAB-2, *Megasphaera* Type 1, and (4) vly gene of *G. vaginalis*, and oligonucleotide probes that can specifically hybridizes to (1) tef1 gene regions of *C. albicans, C. dubliniensis, C. tropicalis, C. parapsilosis, C. krusei*, and *C. glabrata*, (2) AP-65 gene region of *T. vaginalis*, (3) 16S rRNA gene regions of *Atopobium vaginae*, BVAB-2, *Megasphaera* Type 1, and (4) vly gene region of *G. vaginalis* under standard nucleic acid amplification conditions and/or stringent hybridization conditions. As described herein, the sample can be contacted with all of the primers and probes at once, or can be contacted with some of the primers and probes first and subsequently contacted by the remainder of the primers and probes. In some embodiments, the sample is contacted with the primers that can specifically hybridize and amplify (1) tef1 genes of *C. albicans, C. dubliniensis, C. tropicalis, C. parapsilosis, C. krusei*, and *C. glabrata*, and (2) AP-65 gene of *Trichomonas vaginalis*, and the probes that can specifically hybridizes to (1) tef1 gene regions of *C. albicans, C. dubliniensis, C. tropicalis, C. parapsilosis, C. krusei*, and *C. glabrata*, and (2) AP-65 gene region of *T. vaginalis*. In some embodiments, the sample is contacted with the primers that can specifically hybridize and amplify 16S rRNA genes of *Atopobium vaginae*, BVAB-2, *Megasphaera* Type 1, and vly gene of *G. vaginalis*, and the probes that can specifically hybridizes to 16S rRNA genes of *Atopobium vaginae*, BVAB-2, *Megasphaera* Type 1, and vly gene of *G. vaginalis*.

The oligonucleotide probe can be, for example, between about 10 and about 45 nucleotides in length, and comprises a detectable moiety. In some embodiments, the contacting is performed under conditions allowing for the specific hybridization of the primers to the corresponding targeted gene region if the target organism is present in the sample. The presence and/or amount of probe that is specifically bound to the corresponding targeted gene region (if present in the sample being tested) can be determined, wherein bound probe is indicative of the presence of the corresponding target organism in the sample. In some embodiments, the amount of bound probe is used to determine the amount of the corresponding target organism in the sample.

The determining step can be achieved using any methods known to those skilled in the art, including but not limited to, in situ hybridization, following the contacting step. The detection of hybrid duplexes (i.e., of a probe specifically bound to the targeted gene region) can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample. Those of skill in the art will appreciate that wash steps may be employed to wash away excess sample/target nucleic acids or oligonucleotide probe (as well as unbound conjugate, where applicable).

Further, standard heterogeneous assay formats are suitable for detecting the hybrids using the labels present on the oligonucleotide primers and probes.

Some embodiments provide a method to detect a plurality of BV-related bacteria in a biological sample, wherein the method comprises: contacting the biological sample with a plurality of pairs of primers, wherein the plurality of pairs of primer comprises: primers capable of hybridizing to the 16S rRNA genes of *L. crispatus* and *L. jensenii*, wherein each primer comprises a sequence of SEQ ID NO: 14 or SEQ ID NO: 15, or a sequence that exhibits at least about 85% identity to SEQ ID NO: 14 or SEQ ID NO: 15; primers capable of hybridizing to the 16S rRNA gene of BVAB2, wherein each primer comprises a sequence of SEQ ID NO: 4 or SEQ ID NO: 5 or a sequence that exhibits at least about 85% identity to SEQ ID NO: 4 or SEQ ID NO: 5; primers capable of hybridizing to the 16S rRNA gene of *Megasphaera* type 1, wherein each primer comprises a sequence of SEQ ID NO: 7 or SEQ ID NO: 8 or a sequence that exhibits at least about 85% identity to SEQ ID NO: 7 or SEQ ID NO: 8; primers capable of hybridizing to the vly gene of *G. vaginalis*, wherein each primer comprises a sequence selected from the group consisting of SEQ ID NOS: 10-12 or a sequence that exhibits at least about 85% identity to a sequence selected from the group consisting of SEQ ID NOS: 10-12, and primers capable of hybridizing to the 16S rRNA gene of *Atopobium vaginae*, wherein each primer comprises a sequence of SEQ ID NO: 1 or SEQ ID NO: 2, or sequence that exhibits at least about 85% identity to SEQ ID NO: 1 or SEQ ID NO: 2; generating amplicons of the 16S rRNA sequences of *Atopobium vaginae*, BVAB2, *Megasphaera* type 1, and/or *L. crispatus* and *L. jensenii*, and/or amplicons of the vly gene sequence of *G. vaginalis* from said biological sample, if said sample comprises one or more of the BV-related bacteria; and determining the presence or amount of one or more amplified products as an indication of the presence of BV-related bacteria in said biological sample.

In some embodiments, the plurality of pairs of primers comprises a primer comprising the sequence of SEQ ID NO: 1, a primer comprising the sequence of SEQ ID NO: 2, a primer comprising the sequence of SEQ ID NO: 4, a primer comprising the sequence of SEQ ID NO: 5, a primer comprising the sequence of SEQ ID NO: 7, a primer comprising the sequence of SEQ ID NO: 8, a primer comprising the sequence of SEQ ID NO: 10, a primer comprising the sequence of SEQ ID NO: 11, a primer comprising the sequence of SEQ ID NO: 12, a primer comprising the sequence of SEQ ID NO: 14, and a primer comprising the sequence of SEQ ID NO: 15. In some embodiments, the primers capable of hybridizing to the 16S rRNA genes of *Lactobacillus crispatus* and *Lactobacillus jensenii* comprise SEQ ID NOs: 1 and 2; the primers capable of hybridizing to the 16S rRNA gene of BVAB2 comprise SEQ ID NOs: 4 and 5; the primers capable of hybridizing to the 16S rRNA gene of *Megasphaera* type 1 comprise SEQ ID NOs: 7 and 8; the primers capable of hybridizing to the vly gene of *G. vaginalis* comprise: (a) SEQ ID NOs: 10 and 12, (b) SEQ ID NOs: 11 and 12, or a combination thereof, and the primers capable of hybridizing to the 16S rRNA gene of *Atopobium vaginae* comprises SEQ ID NOs: 1 and 2.

In some embodiments, determining the presence or amount of one or more amplified products comprises contacting the amplified products with a plurality of oligonucleotide probes, wherein each of the plurality of oligonucleotide probes comprises a sequence selected from the group consisting of SEQ ID NOs: 3, 6, 9, 13, and 16, or a sequence that exhibits at least about 85% identity to a sequence selected from the group consisting of SEQ ID NOs: 3, 6, 9, 13, and 16. For example, each probe can comprise, or consists of, a sequence selected from the group consisting of SEQ ID NOs: 3, 6, 9, 13, and 16.

Also disclosed herein is a method to detect VVC-associated *Candida* species and *T. vaginalis* in a biological sample, wherein the method comprises: contacting the biological sample with a plurality of pairs of primers, wherein the plurality of pairs of primer comprises: primers capable of hybridizing to the tef1 gene of *C. glabrata*, wherein each primer comprises a sequence of SEQ ID NO: 20 or SEQ ID NO: 21 or a sequence that exhibits at least about 85% identity to SEQ ID NO: 20 or SEQ ID NO: 21; primers capable of hybridizing to the tef1 gene of at least one of *C. albicans, C. tropicalis, C. dubliniensis*, and *C. parapsilosis*, wherein each primer comprises a sequence of SEQ ID NO: 23, SEQ ID NO: 24, or SEQ ID NO: 25, or a sequence that exhibits at least about 85% identity to SEQ ID NO: 23, SEQ ID NO: 24, or SEQ ID NO: 25; primers capable of hybridizing to the tef1 gene of *C. krusei*, wherein each primer comprises a sequence of SEQ ID NO: 27 or SEQ ID NO: 28, or sequence that exhibits at least about 85% identity to SEQ ID NO: 27 or SEQ ID NO: 28; and primers capable of hybridizing to the AP-65 gene of *T. vaginalis*, wherein each primer comprises a sequence of SEQ ID NO: 17 or SEQ ID NO: 18, or sequence that exhibits at least about 85% identity to SEQ ID NO: 17 or SEQ ID NO: 18; and generating amplicons of the tef1 sequences of the *Candida* species and/or amplicons of the AP-65 gene sequence of *T. vaginalis* from said biological sample, if said sample comprises one or more of the VVC-associated *Candida* species and/or *T. vaginalis*; determining the presence or amount of one or more amplified products as an indication of the presence of VVC-associated *Candida* species and *T. vaginalis* in said biological sample.

In some embodiments, the plurality of pairs of primers comprises a primer comprising the sequence of SEQ ID NO: 20, a primer comprising the sequence of SEQ ID NO: 21, a primer comprising the sequence of SEQ ID NO: 23, a primer comprising the sequence of SEQ ID NO: 24, a primer comprising the sequence of SEQ ID NO: 25, a primer comprising the sequence of SEQ ID NO: 27, a primer comprising the sequence of SEQ ID NO: 28, a primer comprising the sequence of SEQ ID NO: 17, and a primer comprising the sequence of SEQ ID NO: 18.

In some embodiments, the primers capable of hybridizing to the tef1 gene of *C. glabrata* comprise SEQ ID NOs: 20 and 21; the primers capable of hybridizing to the tef1 gene of at least one of *C. albicans, C. tropicalis, C. dubliniensis*, and *C. parapsilosis* comprise: (a) SEQ ID NOs: 23 and 24, (b) SEQ ID NOs: 23 and 35, or (c) a combination thereof, the primers capable of hybridizing to the tef1 gene of *C. krusei* comprise of SEQ ID NOs: 27 and 28; and the primers capable of hybridizing to the 16S rRNA gene of *T. vaginalis* comprise SEQ ID NOs: 17 and 18.

In some embodiments, determining the presence or amount of one or more amplified products comprises contacting the amplified products with a plurality of oligonucleotide probes, wherein each of the plurality of oligonucleotide probes comprises a sequence selected from the group consisting of SEQ ID NOs: 3, 6, 9, 13, and 16, or a sequence that exhibits at least about 85% identity to a sequence selected from the group consisting of SEQ ID NOs: 3, 6, 9, 13, and 16. In some embodiments, each of the plurality of oligonucleotide probes comprises, or consists of, a sequence selected from the group consisting of SEQ ID NOs: 3, 6, 9, 13, and 16.

As described herein, the amplification can be carried out by real-time PCR, for example, quantitative real-time PCR (QRT-PCR). The primers suitable for use in the methods and compositions described herein can comprise exogenous nucleotide sequence which allows post-amplification manipulation of amplification products without a significant effect on amplification itself. In some embodiments, the primer can be flanked by complementary sequences comprising a fluorophore at the 5' end, and a fluorescence quencher at the 3' end.

The oligonucleotide probes disclosed herein can comprise a fluorescence emitter moiety and a fluorescence quencher moiety The methods disclosed herein are amendable to automation, thereby providing a high-throughput option for the detection and/or quantification of VVC-associated *Candida* species, *T. vaginalis*, and BV-related bacteria in a sample. Various multiplex PCR platforms, e.g., BD MAX™, Viper™, or Viper™ LT platforms, can be used to perform one or more steps of the disclosed methods. The methods can be performed in a multiplex fashion. For example, the nucleic acid amplification and/or detection, in some embodiments, comprise performing multiplex PCR.

EXAMPLES

The following examples are provided to demonstrate particular situations and settings in which this technology may be applied and are not intended to restrict the scope of the invention and the claims included in this disclosure.

Example 1

Detection of VVC, Trichomoniasis and BV in Vaginal Swab Samples

The study described in this example shows the detection of *Candida* species associated with VVC, trichomoniasis and BV using an automated qualitative in vitro diagnostic test in vaginal swab samples. The test utilizes real time PCR for the amplification of DNA targets and fluorogenic hybridization probes for the detection and identification of target organisms.

Vaginal swabs were collected from women with clinical symptoms of vaginitis/vaginosis. Vaginal specimens were characterized by In Pouch™ TV for *T. vaginalis* while culture followed by BD Phoenix™ identification was used for *Candida* species and the Nugent score (Nugen et al., J. Clin. Microbiol. 29(2):297-301 (1991)), as reference method for BV. Amsel's criteria (Amsel et al., Am. J. Med. 74(1): 14-22 (1983)) were used only in determination of BV statuses for specimens with intermediate Nugent score (Nugent's score 4-6). Three swabs were for test on the BD MAX™ System (Becton, Dickinson and Company, New Jersey) for detection of trichomoniasis, *Candida* species associated with VVC, and BV using a Receiver Operating Characteristic (ROC) curve analysis. The diagnosis of BV was determined using an algorithm based on PCR parameters for the detection of BV-related bacteria, including *Lactobacillus* species, *G. vaginalis*, *Atopobium vaginae*, BVAB-2, and *Megasphaera*-1.

Real-time PCR for the amplification of DNA targets was performed using the primers provided in Table 1 and fluorogenic hybridization probes provided in Table 1 were used to detect *Candida* species associated with VVC, *T. vaginalis*, and BV-related bacteria *L. crispatus*, *L. jensenii*, *G. vaginalis*, *Atopobium vaginae*, *Megasphaera* Type 1, and BVAB2 in each of the vaginal swab samples.

An inclusivity study was performed with cultivable strains originating from 12 countries. The inclusivity study analysis was based on positive/negative status of each individual target according to established PCR parameter thresholds. As shown in Table 2, the assay is capable of detecting a large diversity of strains belonging to species involved in VVC, trichomoniasis and BV. The level of detection of specific organisms in mixtures demonstrated a high level of analytical sensitivity, indicating that clinicians can be able to obtain a clear identification of the pathogen(s) involved in vaginal infection and select the treatment using only one vaginal specimen.

TABLE 2

Inclusivity Study

| Microorganism (Load/swab) | Strain[a] | Origin | Status |
|---|---|---|---|
| Candida albicans (5.4 × 10$^5$ CFU/swab) | ATCC 18804 | Uruguay | POS |
| | ATCC 36232 | ND | POS |
| | ATCC 60193 | USA | POS |
| | ATCC 32032 | South Africa | POS |
| | CCUG 44014 | Sweden | POS |
| Atopobium vaginae (1.1 × 10$^3$ CFU/swab) | CCUG 43049 | Sweden | POS |
| | CCUG 44156 | Sweden | POS |
| | CCUG 55226 | Belgium | POS |
| | CCUG 44258 | Sweden | POS |
| | CCUG 48515 | Sweden | POS |
| Trichomonas vaginalis (1.4 × 10$^3$ Cells/swab) | ATCC 30001 | ND | POS |
| | ATCC 30092 | USA | POS |
| | ATCC 30185 | USA | POS |
| | ATCC 30184 | USA | POS |
| | ATCC 30237 | USA | POS |
| Candida glabrata (2.8 × 10$^4$ CFU/swab) | ATCC 2001 | ND | POS |
| | ATCC 15545 | ND | POS |
| | ATCC 90876 | Germany | POS |
| | YST-192[b] | USA | POS |
| | ATCC MYA-276 | Scotland | POS |
| Candida krusei (3.4 × 10$^4$ CFU/swab) | ATCC 6258 | Sri Lanka | POS |
| | ATCC 28870 | Italy | POS |
| | ATCC 32672 | New Zealand | POS |
| | ATCC 44507 | England | POS |
| | YST-367[b] | USA | POS |
| Gardnerella vaginalis (3.4 × 10$^4$ CFU/swab) | ATCC 14018 | USA | POS |
| | ATCC 14019 | ND | POS |
| | CCUG 44111 | Sweden | POS |
| | CCUG 44159 | Sweden | POS |
| | CCUG 60143 A | Sweden | POS |
| | ATCC 49145 | ND | POS |
| | CCUG 44280 | Sweden | POS |
| Lactobacillus crispatus (1.4 × 10$^4$ CFU/swab) | ATCC 33820 | ND | POS |
| | CCUG 44073 | Sweden | POS |
| | CCUG 42898 | ND | POS |
| | ATCC 33197 | ND | POS |
| | ATCC 53545 | ND | POS |
| Lactobacillus jensenii (2.1 × 10$^3$ CFU/swab) | ATCC 25258 | ND | POS |
| | CCUG 44492 | South Africa | POS |
| | CCUG 44003 | Sweden | POS |
| | CCUG 44122 | Sweden | POS |
| | CCUG 44495 | South Africa | POS |
| Candida parapsilosis (5.4 × 10$^5$ CFU/swab) | ATCC 22019 | Puerto Rico | POS |
| | ATCC 28475 | Norway | POS |
| | YST-100[b] | Germany | POS |
| | CCUG 37233 | Sweden | POS |
| | YST-194 | USA | POS |
| Candida tropicalis (5.4 × 10$^5$ CFU/swab) | ATCC 750 | ND | POS |
| | ATCC 1369 | ND | POS |
| | ATCC 9968 | former USSR | POS |
| | YST-1051[b] | USA | POS |
| | CCUG 21298 | Sweden | POS |

[a]One strain from each microorganism tested in each mix
[b]Strain from BD collection
ND: not determined In simulated co-infection studies, low load of *T. vaginalis* or a low load of *C. glabrata* and *C. krusei* were tested in presence of high loads of *C. albicans*; and low load of *T. vaginalis* was tested in presence of a high load of *C. glabrata*. For each study above, simulated matrix was used rather than vaginal matrix due to the presence of some targets in vaginal flora from asymptomatic/symptomatic women. The results of the simulated co-infection studies are shown in Table 3.

TABLE 3

Stimulated co-infection study of the vaginal panel

| High load (Organisms/ swab) | *Candida albicans* (2.8E+6) | | *Candida glabrata* (2.8E+6) | |
|---|---|---|---|---|
| Low load (Organisms/ swab) | *Candida krusei* (3.4E+4) | *Trichomonas vaginalis* (1.4E+3) | *Candida glabrata* (4.2E+3) | *Trichomonas vaginalis* (1.4E+3) |
| % of conforming Assay results | 95% | 100% | 100% | 100% |

Clinical specimens were defined as positive/negative sample for *Candida* species and *T. vaginalis*. The results of the performance study shown in Table 4 demonstrate that the vaginal panel disclosed herein can be used to detect *T. vaginalis* and *Candida* species with high sensitivity and specificity.

TABLE 4

Performance study for TV and Candida species

| Vaginal panel assay | Reference method | Sensitivity/ Specificity[a] | Fraction[b] | % | [2-sided 95 CI][e] |
|---|---|---|---|---|---|
| T. vaginalis | Inpouch TV™ | Sensitivity | 34/36 | 94.4 | [81.3-99.3] |
| | | Specificity | 729/729 | 100.0 | [99.6-100.0] |
| Candida species[c, d] | BD Phoenix™ | Sensitivity | 171/197 | 86.8 | [81.3-91.2] |
| | | Specificity | 544/568 | 95.8 | [93.8-97.3] |

[a]Sensitivity = True POS/Total POS from reference method and Specificity = True NEG/Total NEG from reference method
[b]«Unresolved» non-reportable results were excluded from Sensitivity/Specificity calculation «1 %)
[c]*Candida* species: *C. albicans*, *C. dubliniensis*, *C. guilliermondii*, *C. tropicalis*, and *C. parapsilosis*
[d]*Candida glabrata* and *Candida krusei* are detected in two distinct channels: eight *C. glabrata* positive specimens for PCR and reference method, one positive for peR and two positive for reference method separately were obtained. One *C. krusei* positive specimen for PCR and reference method and one positive for each method separately were obtained.
[e]2-sided 95% CI was calculated using the Clopper-Pearson method Assay performance for detection of BV was established using a Receiver Operating Characteristic (ROC) curve analysis. Using PCR metrics from the amplification and detection of *Lactobacillus* species, g. *vaginalis, Atopobium vaginae*, BVAB-2 and *Megasphaera*-1, a logistic regression model-based algorithm was built to estimate BV positive probability and give a single BV positive or BV negative call. Patients were considered to have BV if their estimated probability exceeds a threshold determined by ROC curve analysis.

As shown in Table 5, preliminary assay performance results (sensitivity/specificity) based on analysis of 771 total characterized clinical samples was 91.9% (sensitivity)/86.2% (specificity) or increased to 95.4(sensitivity)/92.5% (specificity) when intermediate Nugent Score and Amsel's criteria results were not considered.

TABLE 5

Performance study for BV detection

| New BV Assay | Reference Method | Sensitivity/ Specificity[a] | Fraction[b] | % | [2-sided 95% CI] |
|---|---|---|---|---|---|
| BV | Nugent score/Amsel's criteria | Sensitivity Specificity | 350/381 330/383 | 91.9 86.2 | [88.7-94.4] [82.3-89.5] |
| BV | Nugent score/Amsel's criteria | Sensitivity Specificity | 311/326[c] 297/321[d] | 95.4 92.5 | [92.5-97.4] [89.1-95.2] |

[a]Sensitivity = True POS/Total POS from reference method and Specificity = True NEG/Total NEG from reference method
[b]«Unresolved» non-reportable results were excluded from Sensitivity/Specificity calculation (<1%)
[c]55 specimens with intermediate Nugent Score and classified as POS by Amsel's criteria were excluded.
[d]62 specimens with intermediate Nugent Score and classified as NEG by Amsel's criteria were excluded.

This example demonstrates that the compositions and methods disclosed herein can be used to detect organisms related to VVC, TV, and BV with high specificity and sensitivity.

Example 2

Selection of Primers and Probes for Multiplex Detection of VVC, Trichomoniasis and BV in Vaginal Samples Various primers and probes have been designed and tested for their performance in amplification and detection of VVC-associated *Candida* species, *T. vaginalis*, and BV individually or in a multiplex fashion. Table 6a and 6b provide various primers, primer pairs, and probes that were not selected because of a number of undesired properties, including weak signal, lack of amplification, large size of amplicon, false positive signal, non-specific detection, sensitivity to temperature variation, failure to detect large number of variant strains, limitations in multiplex assay, selective of partner primers/probes, interaction with other primers/probes. Surprisingly, as described in Example 1, a number of primers and probes were found to perform well in the amplification and detection of VVC-associated *Candida* species, *T. vaginalis*, and BV individually or in a multiplex fashion. The superior properties of those primers, probes and some combination thereof were unpredicted. Moreover, the ability of the oligonucleotides of SEQ ID NOs: 1-16 to effectively perform (i.e., specifically amplify and detect target DNA) in a multiplex real-time PCR reaction was not predicted. Similarly, the ability of the oligonucleotides of SEQ ID NOs: 17-29 to effectively perform (i.e., specifically amplify and detect target DNA) in a multiplex real-time PCR reaction also was not predicted.

TABLE 6a

Non-selected primers and probes for detection of BV

| Analyte (target organism) | Targeted gene | Non-selected primers, primer pairs and probes | Primer and probe sequences (5'-3') |
|---|---|---|---|
| *Atopobium vaginae* | 16S rRNA | HINAVFW | GTTAGGTCAGGAGTTAAATCTG (SEQ ID NO: 33) |
| | | HINAVRV | TCATGGCCCAGAAGACC (SEQ ID NO: 34) |
| | | HINAV-RVA | TCGTGGCCCAGAAGGCC (SEQ ID NO: 35) |
| | | AVFP-BV1 | CCCTGGTAGTCCTAGCT (SEQ ID NO: 36) |
| | | AVFP-BV1A* | CCCTGGTAGTCCTAGCC (SEQ ID NO: 37) |
| | | AVRP-BV1 | CGGCACGGAAAGTATAATCT (SEQ ID NO: 38) |
| | | Forward primer (FW): | GGTGAAGCAGTGGAAACACT (SEQ ID NO: 39) |
| | | ATOVAGRT3FW | GCAGCCCAGGACATAAGG (SEQ ID NO: 41) |
| | | Reverse primer (RV): | ATTCGCTTCTGCTCGCGCA (SEQ ID NO: 42) |
| | | MCF-AV-R2 | |
| | | RV: ATOVAGRT3REV* | |
| | | FW: ATOP-442F | GCAGGGACGAGGCCGCAA (SEQ ID NO: 43) |
| | | RV: HINAVRV | TCATGGCCCAGAAGACC (SEQ ID NO: 44) |
| | | FW: MCF-AV-F1, and | CGGATTCATTGGGCGTAAA (SEQ ID NO: 45) |
| | | RV: MCF-AV-R3 | CGCCTCAGCGTCAGT (SEQ ID NO: 46) |
| | | FW: MCF-AV-F1, and | CGGATTCATTGGGCGTAAA (SEQ ID NO: 47) |
| | | RV: MCF-AV-R4 | ACACCTAGTGTCCATCGTTTA (SEQ ID NO: 48) |
| | | FW: MCF-AV-F2, and | CCTTCGGGTTGTAAACCG (SEQ ID NO: 49) |
| | | RV: MCF-AV-R3 | CGCCTCAGCGTCAGT (SEQ ID NO: 50) |
| BVAB2 | 16S | FW: HINBVAB2FW, and | AGGCGGCTAGATAAGTGTGA (SEQ ID NO: 51) |
| | | RV: HINBVAB2RV | TCCTCTCCAGCACTCAAGCTAA (SEQ ID NO: 52) |
| | | FW: BVAB2-619F, and | TTAACCTTGGGGTTCATTACAA (SEQ ID NO: 53) |
| | | RV: BVAB2-1024R | AATTCAGTCTCCTGAATCGTCAGA (SEQ ID NO: 54) |
| | | FW: BVAB2_585FA | GCGGCTAGATAAGTGTGATGTTT (SEQ ID NO: 4) |
| | | FW: HINBVAB2FW | AGGCGGCTAGATAAGTGTGA (SEQ ID NO: 55) |
| | | FW: BVABPP-BV2 | CGTGTAGGCGGCTAGATAAGTG (SEQ ID NO: 56) |
| | | RV: BVAB2_879R | GAATACTTATTGTGTTAACTGCGC (SEQ ID NO: 57) |
| *Megasphaera* type 1 | 16S | FW: HINMGSTYP1FW, and | GACGGATGCCAACAGTATCCGTCCG (SEQ ID NO: 7) |
| | | RV: HINMGSTYP1RV | AAGTTCGACAGTTTCCGTCCCCTC (SEQ ID NO: 58) |
| *Gardnerella vaginalis* | vaginolysin (vly) | FW: GVVLYFW1, and | GGCGGCGAAAGTGCTGTA (SEQ ID NO: 59) |
| | | RV: GVVLYRV1 | AGCCGTTCACTGCGGAAGT (SEQ ID NO: 12) |
| | | FW: GVVLYFW2, and | GCCAACGATGATCGCGTAT (SEQ ID NO: 10) |
| | | RV: GVVLYRV2A | CAAGCTCGGCATGTTATCCAT (SEQ ID NO: 60) |
| | | FW: MCF-GV-F6 | CCAGAATTTGATGGATAACATGCC (SEQ ID NO: 65) |
| | | FW: MCF-GV-F7 | ATGGACAATATGCCAAGCCT (SEQ ID NO: 66) |
| | | RV: MCF-GV-R2 | TTCACTGCGGAAGTTACAGA (SEQ ID NO: 67) |
| | | RV: MCF-GV-R3 | TTAACTGCGGAAGTAACGGA (SEQ ID NO: 68) |
| | | RV: MCF-GV-R4 | TTAACTGCTGAAGTAACGGA (SEQ ID NO: 69) |
| | | Probes (5' fluorophore: Cy5; 3' fluorophore: BHQ2): | ACAGCACTTTCGCCGCC (SEQ ID NO: 13) |
| | | MCF-GV-T3-CY5-B2 | ACAGCACTCTCGCCGCC (SEQ ID NO: 70) |
| | | MCF-GV-T4-CY5-B2 | |
| *Gardnerella vaginalis* | 16S rRNA | FW: HINGVFW, and | GGAAACGGGTGGTAATGCTGG (SEQ ID NO: 61) |
| | | RV: HINGVRV | CGAAGCCTAGGTGGGCCATT (SEQ ID NO: 62) |
| | | FW: GV1FW, and | TTACTGGTGTATCACTGTAAGG (SEQ ID NO: 63) |
| | | RV: GV3RV | CCGTCACAGGCTGAACAGT (SEQ ID NO: 64) |
| *Lactobacillus crispatus* | 16S rRNA | FW: L.crisp-452F, and | GATAGAGGTAGTAACTGGCCTTTA (SEQ ID NO: 71) |
| | | RV: L.crisp-1023R | CTTTGTATCTCTACAAATGCACTA (SEQ ID NO: 72) |
| | | FW: HIN LG FW, and | CGAGCTTGCCTAGATGAATTTG (SEQ ID NO: 73) |
| | | RV: HIN LG RV | CTCTAGACATGCGTCTAGTG (SEQ ID NO: 74) |
| | | FW: HIN LC FW, and | GATTTACTTCGGTAATGACGTTAGGA (SEQ ID NO: 75) |
| | | RV: HIN LC RV | AGCTGATCATGCGATCTGCTTTC (SEQ ID NO: 76) |
| | | FW: HIN LJ FW | GCCTATAGAAATTCTTCGGAATGGACA (SEQ ID NO: 77) |
| | | RV: HIN LJ RV | CAAATGGTATCCCAGACTTAAGGG (SEQ ID NO: 78) |
| | | FW: MEG-LG_LJ-F6 | GTCGAGCGAGCTTGCCTA (SEQ ID NO: 79) |
| | | FW: MCF-LC-F4 | GAACTAACAGATTTACTTCGGTAATG (SEQ ID NO: 80) |
| | | RV: MCF-LG-R3 | AAACTCTAGACATGCGTCTAGT (SEQ ID NO: 81) |
| | | RV: MCF-LJ_LC-R1 | GTTTCCAAATGGTATCCCAGA (SEQ ID NO: 82) |
| | | Probes: MCF-Lj-Lc-T1_ROX-B2 | Probes: CGGCGGATGGGTGAGTAAC (SEQ ID NO: 103) |
| | | MCF-Lg-T5_ROX-B2 | CCAAGAGACTGGGATAACACCTG (SEQ ID NO: 105) |
| | | MCF-Lj-T7_ROX-B2 | TCTTCGGAATGGACATAGATACAAGCTA (SEQ ID NO: 115) |
| | | MCF-Lc-T3_ROX-B2 | ATCCGCCGTCTGCTTT (SEQ ID NO: 116) |
| | | FW: MCF-LG-F5 | GCCTAGATGAATTTGGTGCTT (SEQ ID NO: 83) |
| | | FW: MCF-LJ-F6 | CGAGCTTGCCTATAGAAATTCTT (SEQ ID NO: 84) |
| | | FW: MCF-LC-F4 | GAACTAACAGATTTACTTCGGTAATG (SEQ ID NO: 85) |
| | | RV: MCF-LG-R3 | AAACTCTAGACATGCGTCTAGT (SEQ ID NO: 86) |
| | | RV: MCF-LJ_LC-R1 | GTTTCCAAATGGTATCCCAGA (SEQ ID NO: 87) |

TABLE 6a-continued

Non-selected primers and probes for detection of BV

| Analyte (target organism) | Targeted gene | Non-selected primers, primer pairs and probes | Primer and probe sequences (5'-3') |
|---|---|---|---|
| | | Probes:<br>MCF-Lj-Lc-T1_ROX-B2<br>MCF-Lg-T5_ROX-B2<br>FW: MCF-LJ_LC-F8<br>FW: MCF-LG-F9<br>RV: MCF-LSP-R6<br>Primers:<br>MCF-Lj_Lc-F8<br>MCF-Lg-F9<br>MCF-Lj_Lc-R7<br>Probes: (5' fluorophore: ROX; 3' fluorophore: BHQ2):<br>MCF-LSP-T8_ROX-B2<br>MCF-LSP-T11_ROX-B2<br>MCF-LSP-T13_ROX-B2<br>MCF-LJ_LC-T15_ROX-B2<br>MCF-LG-T16_ROX-B2<br>FW: HIN LG FW<br>FW: HIN LJ FW<br>FW: HIN LC FW<br>RV: HIN LG RV<br>RV: HIN LJ RV<br>RV: HIN LC RV<br>Probes (5' fluorophore: ROX; 3' fluorophore: BHQ2):<br>MCF-Lj-Lc-T1_ROX-B2<br>MCF-Lg-T5_ROX-B2 | Probes:<br>CGGCGGATGGGTGAGTAAC (SEQ ID NO: 103)<br>CCAAGAGACTGGGATAACACCTG (SEQ ID NO: 105)<br>TTAAAAGGCGGCGTAAGC (SEQ ID NO: 14)<br>ACTAGACGCATGTCTAGAGTTT (SEQ ID NO: 88)<br>GCCAGTTACTACCTCTATC (SEQ ID NO: 15)<br>TGCATTAGCTAGTTGGTAAGGTAAC (SEQ ID NO: 89)<br>Primers:<br>TTAAAAGGCGGCGTAAGC (SEQ ID NO: 14)<br>ACTAGACGCATGTCTAGAGTTT (SEQ ID NO: 88)<br>GCCAGTTACTACCTCTATCCT (SEQ ID NO: 15)<br>Probes:<br>AAGTCTGATGGAGCAACGCC (SEQ ID NO: 16)<br>ACATTGGGACTGAGACACGG (SEQ ID NO: 90)<br>AGGCTTACCAAGGCGATGAT (SEQ ID NO: 91)<br>CGGCTTACCAAGGCAATGAT (SEQ ID NO: 92)<br><br>CGAGCTTGCCTAGATGAATTTG (SEQ ID NO: 97)<br>GCCTATAGAAATTCTTCGGAATGGACA (SEQ ID NO: 98)<br>GATTTACTTCGGTAATGACGTTAGGA (SEQ ID NO: 99)<br>CTCTAGACATGCGTCTAGTG (SEQ ID NO: 100)<br>CAAATGGTATCCCAGACTTAAGGG (SEQ ID NO: 101)<br>AGCTGATCATGCGATCTGCTTTC (SEQ ID NO: 102)<br>Probes:<br>CGGCGGATGGGTGAGTAAC (SEQ ID NO: 103)<br>CCAAGAGACTGGGATAACACCTG (SEQ ID NO: 105) |

TABLE 6b

Non-selected primers and probes for detection of VVC and trichomoniasis

| Analyte (target organism) | Targeted gene | Non-selected primers and probes | Primer and probe sequences (5'-3') |
|---|---|---|---|
| Candida albicans | RNase P RNA 1 (RPR1) | FW: cand-CR1<br>RV: cand-CR5<br>Probes:<br>alb-T-FAM-B1<br>cand-T-FAM-B1<br>cand-Ta-FAM-B1 | CGGGTGGGAAATTCGGT (SEQ ID NO: 117)<br>CAATGATCGGTATCGGGT (SEQ ID NO: 118)<br>Probes:<br>CAGCTTGTAGTAAAGAATTACTCAC (SEQ ID NO: 119)<br>TTCGCATATTGCACTAAATAG (SEQ ID NO: 120)<br>TTCGCATATTGCACTAAACAG (SEQ ID NO: 121) |
| Candida albicans | Topoisomerase III | FW: MenCa1377fw<br>RV: MenCa1472rv<br>Probe:<br>MenCa-T-FAM-B1 | CAACGCCAACGAAGACAAG (SEQ ID NO: 122)<br>CCAGCTTTGTTTGCATCAA (SEQ ID NO: 123)<br>Probe:<br>AAAGCCGATGGTAGTAGAAAACTGC (SEQ ID NO: 124) |
| Candida albicans | Topoisomerase II | FW: CABF59<br>RV: CABR110 | TTGAACATCTCCAGTTTCAAAGGT (SEQ ID NO: 125)<br>GTTGGCGTTGGCAATAGCTCTG (SEQ ID NO: 126) |
| Candida species | CHS1 | FW: Jorprimer1Fw<br>RV: Jorprimer2Rv<br>Probes:<br>JorCa-T-FAM-B1<br>JorCpara-T-FAM-B1<br>JorCtro-T-FAM-B1 | CGCCTCTTGATGGTGATGAT (SEQ ID NO: 127)<br>TCCGGTATCACCTGGCTC (SEQ ID NO: 128)<br>Probes:<br>CGTTCGTACTAGAGTTGTGTTGTTTTGGAT (SEQ ID NO: 129)<br>GAGGCTGTGATGTGTGCTGTTGACCAG (SEQ ID NO: 130)<br>AGGCTTGCTCTTTGTCGGGCGAGCGAACG (SEQ ID NO: 131) |
| Candida species | TEF | FW Primers:<br>ECanG278<br>cand-CR1-NP-Ca<br>cand-CR1-NP-CtCp<br>RT-Ca_Cd-F2<br>RT-Ctro-F3<br>RT-Cpara-F4<br>RV Primers:<br>ECanG401<br>ECanG401a | FW Primers:<br>CAGGTCACAGAGATTTCATCAAG (SEQ ID NO: 132)<br>GAAATTCGGTGGTACGCTCC (SEQ ID NO: 133)<br>GAAATTCGGTGGTACTCTCC (SEQ ID NO: 134)<br>GTTGTGACTCTTCAATGCCCAA (SEQ ID NO: 135)<br>GTTGTGACTCTTTCAACGCTCAA (SEQ ID NO: 136)<br>GATGTGACTCCTTCAATGCTCAA (SEQ ID NO: 137)<br>RV Primers:<br>GTAAGCCAACAAAGCGTGTTCTC (SEQ ID NO: 138)<br>GAAAGCCAATAGAGCGTGTTCTC (SEQ ID NO: 139) |

TABLE 6b-continued

Non-selected primers and probes for detection of VVC and trichomoniasis

| Analyte (target organism) | Targeted gene | Non-selected primers and probes | Primer and probe sequences (5'-3') |
|---|---|---|---|
| | | Cand-CR5-NP-CaCt | GATCGGTATCGGGTGCTTG (SEQ ID NO: 140) |
| | | Cand-CR5-NP-Cp | GATCGGTATCGGGTTCTTG (SEQ ID NO: 141) |
| | | RT-Cdub-R4 | CAGCGTCACCGGATTTGAC (SEQ ID NO: 142) |
| | | Probes: | Probes: |
| | | ECanG-TL1-O2-FAM-B1 | TGATTATTGCTGGTGG (SEQ ID NO: 143) |
| | | cand-T-FAM-B1 | TTCGCATATTGCACTAAATAG (SEQ ID NO: 120) |
| | | cand-Ta-FAM-B1 | TTCGCATATTGCACTAAACAG (SEQ ID NO: 121) |
| | | RT-Ca_Cd_Cp-T1-FAM-B1 | TGCTTGTAAATTCGACACTTTG (SEQ ID NO: 144) |
| | | RT-Ctro-T4-FAM-B1 | TGTAAATTCGACACCTTGGTTGA (SEQ ID NO: 145) |
| | | RT-Ca_Cd-T2-FAM-B1 | TTGTAAATTCGACACTTTGGTTG (SEQ ID NO: 146) |
| | | RT-Cpar-T6-FAM-B1 | CGACACTTTGATTGAAAAGATTGAC (SEQ ID NO: 147) |
| Candida species | ITS2 | FW Primers: | FW Primers: |
| | | ITS2-Ca-Fow | GGGTTTGCTTGAAAGACGGTA (SEQ ID NO: 148) |
| | | ITS2-Ctr-Fow | CGTGGTAACTTATTTTAAGCG (SEQ ID NO: 149) |
| | | ITS2-Cpar-Fow | GGGTTTGGTGTTGAGCGATAC (SEQ ID NO: 150) |
| | | RV Primers: | RV Primers: |
| | | ITS2-Ca-Rev | TTGAAGATATACGTGGTGGACGTTA (SEQ ID NO: 151) |
| | | ITS2-Ctr-Rev | GCTTAAGTTCAGCGGGTAGTCCTA (SEQ ID NO: 152) |
| | | ITS2-Cpar-Rev | GGAGTTTGTACCAATGAGTGGAAA (SEQ ID NO: 153) |
| | | Probes: | Probes |
| | | ITS2-Ca-CFO-B1 | ACCTAAGCCATTGTCAAAGCGATCCCG (SEQ ID NO: 154) |
| | | ITS2-Ctr-CFO-B1 | TGGCCACCATTTATTTCATAACTTTGACC (SEQ ID NO: 155) |
| | | ITS2-Cpar-CFO-B1 | CTCCGCCTTTCTTTCAAGCAAACCCAG (SEQ ID NO: 156) |
| Candida glabrata | RNase P RNA 1 (RPR1) | FW Primers: | FW Primers: |
| | | gla-CR3 | GGCAACGGCTGGGAAT (SEQ ID NO: 157) |
| | | gla-CR3a | AGCAACGGCTGGGAAT (SEQ ID NO: 158) |
| | | RV Primer: | RV Primer: |
| | | cand-CR5 | CAATGATCGGTATCGGGT (SEQ ID NO: 159) |
| | | Probe: | Probe: |
| | | gla-T-FAM-B1 | TAAAGCCTCACCACGATTTTGACAC (SEQ ID NO: 160) |
| Candida glabrata | Topoisomerase II | FW Primer: CGBF35 | CCCAAAAATGGCCGTAAGTATG (SEQ ID NO: 161) |
| | | RV Primer: CGBR77 | CTGCTTGAAAGAAATATCGGAGAC (SEQ ID NO: 162) |
| Candida glabrata | CHS1 | FW: Jorprimer1Fw | CGCCTCTTGATGGTGATGAT (SEQ ID NO: 127) |
| | | RV: Jorprimer2Rv | TCCGGTATCACCTGGCTC (SEQ ID NO: 128) |
| | | Probe: | Probe: |
| | | JorCgla-T-FAM-B1 | CGACTGGTTGACGATAATCAGAGGAGATGGG (SEQ ID NO: 163) |
| Candida glabrata | TEF | FW Primers: | Primers: |
| | | RT-Cgla-F5 | ACCCACCAAAGGCTGCT (SEQ ID NO: 164) |
| | | RT-Cgla-F6 | CGACCCACCAAAGGCTGCT (SEQ ID NO: 165) |
| | | Probe: | Probe: |
| | | RT-Cgla-T8-FAM-B1 | ACTGTCACACCGCCCACATT (SEQ ID NO: 166) |
| Candida krusei | RNase P RNA 1 (RPR1) | FW Primers: cand-CR1 | CGGGTGGGAAATTCGGT (SEQ ID NO: 117) |
| | | kru-CR1-SiT | ATAGAGTAGCTCGGTCCC (SEQ ID NO: 167) |
| | | RV Primers: krus-CR5 | TAGTGATCGGTATCGAGTT (SEQ ID NO: 168) |
| | | Kru-CR5-NP2 | CGGTATCGAGTTTCCATG (SEQ ID NO: 169) |
| | | Probe: | Probe: |
| | | krus-T-FAM-B1 | CCAAAGTTGTACAAGCAAGTACCA (SEQ ID NO: 170) |
| Candida krusei | Topoisomerase II (K$_{ANBE}$, 2002) | FW: CKSF35 | GAGCCACGGTAAAGAATACACA (SEQ ID NO: 171) |
| | | RV: CKSR57 | TTTAAAGTGACCCGGATACC (SEQ ID NO: 172) |
| Candida krusei | TEF | RV Primers: RT-Ckru-R5 | CTTTGGATGGTCTTCAACAGA (SEQ ID NO: 173) |
| | | SiT-Ckru-R10 | ATCACCAGACTTGACGG (SEQ ID NO: 174) |
| | | Probes: | Probes: |
| | | SiT-Ckru-T10-CFO-B1 | AGTCTGTTGAAGACCATCCA (SEQ ID NO: 175) |
| | | SiT-Ckru-T9-CFO-B1 | ATGTAAGTTCGACGAATTAATC (SEQ ID NO: 176) |
| TV | Ap65-1 | FW Primers: NP.TV.MAX.FP1 | TCTGGCAAGATCAAGGACAT (SEQ ID NO: 177) |
| | | SiT.TV.MAX.FP1 | GAAGATTCTGGCAAGATCA (SEQ ID NO: 178) |
| | | RV Primers: NP.TV.MAX.RP1 | CATCTGTAACGACAATGCAGC (SEQ ID NO: 179) |
| | | SiT.TV.MAX.RP1 | GACAATGCAGCGGAT (SEQ ID NO: 180) |
| | | Probes: | Probes: |
| | | NP.TV.MAX.D1-T-FAM-B1 | AACTACCCACGCCAGGACAT (SEQ ID NO: 181) |
| | | SiT.TV.MAX.D1-T-FAM-B1 | CCGCAACTACCCACGCCA (SEQ ID NO: 182) |

Tables 7a and 7b provide a number of master mixes of primers and probes that were not selected because of a number of undesired properties, including false positive signal and failure to detect variant strains.

TABLE 7a

Non-selected master mixes for detection of BV

| Master Mix ID | Primers and Probes | Primer and Probe Sequences (5'-3') |
|---|---|---|
| Master Mix I | Primers: | |
| | BVAB2_585Fa | GCGGCTAGATAAGTGTGATGTTT (SEQ ID NO: 4) |
| | BVAB2_666RA | CTCTCCAGCACTCAAGCTAAA (SEQ ID NO: 5) |
| | MCF-LJ_LC-F8 | TTAAAAGGCGGCGTAAGC (SEQ ID NO: 14) |
| | MCF-LG-F9 | ACTAGACGCATGTCTAGAGTTT (SEQ ID NO: 88) |
| | MCF-LSP-R6 | GCCAGTTACTACCTCTATC (SEQ ID NO: 15) |
| | MENAV248FW | CCCTATCCGCTCCTGATACC (SEQ ID NO: 1) |
| | MENAV334RV | CCAAATATCTGCGCATTTCA (SEQ ID NO: 2) |
| | MCF-GV-F6 | CCAGAATTTGATGGATAACATGCC (SEQ ID NO: 65) |
| | MCF-GV-F7 | ATGGACAATATGCCAAGCCT (SEQ ID NO: 66) |
| | MCF-GV-R2 | TTCACTGCGGAAGTTACAGA (SEQ ID NO: 67) |
| | MCF-GV-R4 | TTAACTGCTGAAGTAACGGA (SEQ ID NO: 69) |
| | MEGAE-456F | GATGCCAACAGTATCCGTCCG (SEQ ID NO: 7) |
| | MEGAE-667R | CCTCTCCGACACTCAAGTTCGA (SEQ ID NO: 8) |
| | Probes: | |
| | BVAB2_613_641_FAM-B1 | FAM-CAAGGCTTAACCTTGGGGTTCATTACAA-BHQ1 (SEQ ID NO: 6) |
| | MCF-LSP-T11_ROX-B2 | ROX-AAGTCTGATGGAGCAACGCC-BHQ2 (SEQ ID NO: 16) |
| | MCF-AV-T4_FAM-B1 | FAM-TCCCCTACCAGACTCAAGCCTGC-BHQ1 (SEQ ID NO: 3) |
| | MCF-GV-T3-CY5-B2 | Cy5-ACAGCACTTTCGCCGCC-BHQ2 (SEQ ID NO: 13) |
| | MCF-GV-T4-CY5-B2 | Cy5-ACAGCACTCTCGCCGCC-BHQ2 (SEQ ID NO: 70) |
| | MEGA_485-506-T-HEX-BHQ1 | HEX-GTACCGTAAGAGAAAGCCACGG-BHQ1 (SEQ ID NO: 9) |
| Master Mix II | Primers: | |
| | BVAB2_585Fa | GCGGCTAGATAAGTGTGATGTTT (SEQ ID NO: 4) |
| | BVAB2_666Ra | CTCTCCAGCACTCAAGCTAAA (SEQ ID NO: 5) |
| | MCF-Lj_Lc-F8 | TTAAAAGGCGGCGTAAGC (SEQ ID NO: 14) |
| | MCF-Lg-F9 | ACTAGACGCATGTCTAGAGTTT (SEQ ID NO: 88) |
| | MCF-Lsp-R6 | GCCAGTTACTACCTCTATC (SEQ ID NO: 15) |
| | MenAv248fw | CCCTATCCGCTCCTGATACC (SEQ ID NO: 1) |
| | MenAv334rv | CCAAATATCTGCGCATTTCA (SEQ ID NO: 2) |
| | MenGV981fw, | CGCATCTGCTAAGGATGTTG (SEQ ID NO: 106) |
| | MenGV1072rv | CAGCAATCTTTTCGCCAACT (SEQ ID NO: 107) |
| | MegaE-456F | GATGCCAACAGTATCCGTCCG (SEQ ID NO: 7) |
| | MegaE-667R | CCTCTCCGACACTCAAGTTCGA (SEQ ID NO: 8) |
| | Probes: | |
| | BVAB2_613_641_CFO-B1 | FAM-CAAGGCTTAACCTTGGGGTTCATTACAA-BHQ1 (SEQ ID NO: 6) |
| | MCF-Lsp-T11_ROX-B2 | ROX-AAGTCTGATGGAGCAACGCC-BHQ2 (SEQ ID NO: 16) |
| | MCF-Av-T4_FAM-B1 | FAM-TCCCCTACCAGACTCAAGCCTGC-BHQ1 (SEQ ID NO: 3) |
| | MenGV-T-ROX-B2 | ROX-TGCAACTATTTCTGCAGCAGATCC-BHQ2 (SEQ ID NO: 108) |
| | Mega_485-506-T-CFO-BHQ1 | CFO-GTACCGTAAGAGAAAGCCACGG-BHQ1 (SEQ ID NO: 9) |
| Master Mix IIII | Primers: | |
| | BVAB2_585Fa | GCGGCTAGATAAGTGTGATGTTT (SEQ ID NO: 4) |
| | BVAB2_666Ra | CTCTCCAGCACTCAAGCTAAA (SEQ ID NO: 5) |
| | MCF-Lj_Lc-F8 | TTAAAAGGCGGCGTAAGC (SEQ ID NO: 14) |
| | MCF-Lg-F9 | ACTAGACGCATGTCTAGAGTTT (SEQ ID NO: 88) |
| | MCF-Lsp-R6 | GCCAGTTACTACCTCTATC (SEQ ID NO: 15) |
| | MenAv248fw | CCCTATCCGCTCCTGATACC (SEQ ID NO: 1) |
| | MenAv334rv | CCAAATATCTGCGCATTTCA (SEQ ID NO: 2) |
| | GVvlyfw2 | GCCAACGATGATCGCGTAT (SEQ ID NO: 10) |
| | GVvlyrv2 | CAGGCTTGGCATATTGTCCAT (SEQ ID NO: 109) |
| | GVvlyfw2a | GCCAATAATGACCGCGTAT (SEQ ID NO: 11) |
| | GVvlyrv2a | CAAGCTCGGCATGTTATCCAT (SEQ ID NO: 60) |
| | MegaE-456F | GATGCCAACAGTATCCGTCCG (SEQ ID NO: 7) |
| | MegaE-667R | CCTCTCCGACACTCAAGTTCGA (SEQ ID NO: 8) |
| | Probes: | |
| | BVAB2_613_641_CFO-B1 | FAM-CAAGGCTTAACCTTGGGGTTCATTACAA-BHQ1 (SEQ ID NO: 6) |
| | MCF-Lsp-T11_ROX-B2 | ROX-AAGTCTGATGGAGCAACGCC-BHQ2 (SEQ ID NO: 16) |
| | MCF-Av-T4_FAM-B1 | FAM-TCCCCTACCAGACTCAAGCCTGC-BHQ1 (SEQ ID NO: 3) |
| | GVvly-T2-ROX-B2 | ROX-CCCAGGTGCTCTTTTCCGTGCTGA-BHQ2 (SEQ ID NO: 110) |
| | GVvly-T2a-ROX-B2 | ROX-CCCAGGTGCGCTGTTCCGCGCTGA-BHQ2 (SEQ ID NO: 111) |
| | Mega_485-506-T-CFO-BHQ1 | CFO-GTACCGTAAGAGAAAGCCACGG-BHQ1 (SEQ ID NO: 9) |
| Master Mix IV | Primers: | |
| | BVAB2_585Fa | GCGGCTAGATAAGTGTGATGTTT (SEQ ID NO: 4) |
| | BVAB2_666Ra | CTCTCCAGCACTCAAGCTAAA (SEQ ID NO: 5) |
| | MCF-Lj_Lc-F8 | TTAAAAGGCGGCGTAAGC (SEQ ID NO: 14) |
| | MCF-Lg-F9 | ACTAGACGCATGTCTAGAGTTT (SEQ ID NO: 88) |
| | MCF-Lsp-R6 | GCCAGTTACTACCTCTATC (SEQ ID NO: 15) |
| | MenAv248fw | CCCTATCCGCTCCTGATACC (SEQ ID NO: 1) |
| | MenAv334rv | CCAAATATCTGCGCATTTCA (SEQ ID NO: 2) |
| | GVvlyfw1 | GGCGGCGAAAGTGCTGTA (SEQ ID NO: 59) |
| | | AGCCGTTCACTGCGGAAGT (SEQ ID NO: 12) |

TABLE 7a-continued

Non-selected master mixes for detection of BV

| Master Mix ID | Primers and Probes | Primer and Probe Sequences (5'-3') |
|---|---|---|
| | GVvlyrv1 | GGCGGCGAAAGTGCTGTC (SEQ ID NO: 112) |
| | GVvlyfw1a | GATGCCAACAGTATCCGTCCG (SEQ ID NO: 7) |
| | MegaE-456F | CCTCTCCGACACTCAAGTTCGA (SEQ ID NO: 8) |
| | MegaE-667R | |
| | Probes: | FAM-CAAGGCTTAACCTTGGGGTTCATTACAA-BHQ1 (SEQ ID NO: 6) |
| | BVAB2_613_641_CFO-B1 | ROX-AAGTCTGATGGAGCAACGCC-BHQ2 (SEQ ID NO: 16) |
| | MCF-Lsp-T11_ROX-B2 | FAM-TCCCCTACCAGACTCAAGCCTGC-BHQ1 (SEQ ID NO: 3) |
| | MCF-Av-T4_FAM-B1 | ROX-TTCAGCGCCCAACCAAGAGCTCTGT-BHQ2 (SEQ ID NO: 113) |
| | GVvly-T1-ROX-B2 | ROX-TTAAGCATCCAACTAAGAGCTCTGT-BHQ2 (SEQ ID NO: 114) |
| | Gvvly-T1a-ROX-B2 | CFO-GTACCGTAAGAGAAAGCCACGG-BHQ1 (SEQ ID NO: 9) |
| | Mega_485-506-T-CFO-BHQ1 | |

TABLE 7b

Non-selected master mixes for detection of VVC and trichomoniasis

| Master Mix ID | Primers and Probes | Primer and Probe Sequences (5'-3') |
|---|---|---|
| Master Mix I | SiT-Cgla-F8 | CGAACAATTGACTGAAGGTTTG (SEQ ID NO: 20) |
| | RT-Cgla-R7 | CGGACTTCAAGAACTTTGGAGA (SEQ ID NO: 21) |
| | RT-Cgla-T7-Fam-B1 | CTTGTAAGTTCGAAGAATTGTTGGA (SEQ ID NO: 22) |
| | TV.MAX.FP1 | GAAGATTCTGGCAAGATCAAGGA (SEQ ID NO: 17) |
| | TV.MAX.RP1 | ACGACAATGCAGCGGATGT (SEQ ID NO: 18) |
| | TV.MAX.D1-T-ROX-B2 | ATCCTCCGCAACTACCCACGCCA (SEQ ID NO: 19) |
| | kru-CR1-SiT | ATAGAGTAGCTCGGTCCC (SEQ ID NO: 167) |
| | Kru-CR5-NP2 | CGGTATCGAGTTTCCATG (SEQ ID NO: 169) |
| | krus-T-FAM-B1 | CCAAAGTTGTACAAGCAAGTACCA (SEQ ID NO: 170) |
| | RT-Ca_Cd_Ct-F1 | CCACCAAAGGGTTGTGAC (SEQ ID NO: 23) |
| | RT-Cpara-F4 | GATGTGACTCCTTCAATGCTCAA (SEQ ID NO: 137) |
| | RT-Ca_Ct-R3 | CAGCATCACCGGATTTGAC (SEQ ID NO: 24) |
| | RT-Cpar-R6 | CGGACTTGATGAATTTTGGTTCA (SEQ ID NO: 25) |
| | RT-Cdub-R4 | CAGCGTCACCGGATTTGAC (SEQ ID NO: 142) |
| | RT-Ca_Cd_Cp-T1-FAM-B1 | TGCTTGTAAATTCGACACTTTG (SEQ ID NO: 144) |
| | RT-Ctro-T4-FAM-B1 | TGTAAATTCGACACCTTGGTTGA (SEQ ID NO: 145) |
| Master Mix II | SiT-Cgla-F8 | CGAACAATTGACTGAAGGTTTG (SEQ ID NO: 20) |
| | RT-Cgla-R7 | CGGACTTCAAGAACTTTGGAGA (SEQ ID NO: 21) |
| | RT-Cgla-T7-Fam-B1 | CTTGTAAGTTCGAAGAATTGTTGGA (SEQ ID NO: 22) |
| | TV.MAX.FP1 | GAAGATTCTGGCAAGATCAAGGA (SEQ ID NO: 17) |
| | TV.MAX.RP1 | ACGACAATGCAGCGGATGT (SEQ ID NO: 18) |
| | TV.MAX.D1-T-ROX-B2 | ATCCTCCGCAACTACCCACGCCA (SEQ ID NO: 19) |
| | kru-CR1-SiT | ATAGAGTAGCTCGGTCCC (SEQ ID NO: 167) |
| | Kru-CR5-NP2 | CGGTATCGAGTTTCCATG (SEQ ID NO: 169) |
| | krus-T-FAM-B1 | CCAAAGTTGTACAAGCAAGTACCA (SEQ ID NO: 170) |
| | RT-Ca_Cd-F2 | GTTGTGACTCTTTCAATGCCAA (SEQ ID NO: 135) |
| | RT-Ctro-F3 | GTTGTGACTCTTTCAACGCTCAA (SEQ ID NO: 136) |
| | RT-Cpara-F4 | GATGTGACTCCTTCAATGCTCAA (SEQ ID NO: 137) |
| | RT-Ca_Ct-R3 | CAGCATCACCGGATTTGAC (SEQ ID NO: 24) |
| | RT-Cpar-R6 | CGGACTTGATGAATTTTGGTTCA (SEQ ID NO: 25) |
| | RT-Cdub-R4 | CAGCGTCACCGGATTTGAC (SEQ ID NO: 142) |
| | RT-Ca_Cd-T3-FAM-B1 | TGCTTGTAAATTCGACACTTTGGTTG (SEQ ID NO: 26) |
| | RT-Ctro-T4-FAM-B1 | TGTAAATTCGACACCTTGGTTGA (SEQ ID NO: 145) |
| | RT-Cpar-T6-FAM-B1 | CGACACTTTGATTGAAAAGATTGAC (SEQ ID NO: 147) |
| Master Mix III | SiT-Cgla-F8 | CGAACAATTGACTGAAGGTTTG (SEQ ID NO: 20) |
| | RT-Cgla-R7 | CGGACTTCAAGAACTTTGGAGA (SEQ ID NO: 21) |
| | RT-Cgla-T7-Fam-B1 | CTTGTAAGTTCGAAGAATTGTTGGA (SEQ ID NO: 22) |
| | TV.MAX.FP1 | GAAGATTCTGGCAAGATCAAGGA (SEQ ID NO: 17) |
| | TV.MAX.RP1 | ACGACAATGCAGCGGATGT (SEQ ID NO: 18) |
| | TV.MAX.D1-T-ROX-B2 | ATCCTCCGCAACTACCCACGCCA (SEQ ID NO: 19) |
| | RT-Ckru-F7 | GCAGCTTCCTTCAATGCTCAA (SEQ ID NO: 27) |
| | RT-Ckru-R5 | CTTTGGATGGTCTTCAACAGA (SEQ ID NO: 173) |
| | RT-Ckru-T9-FAM-B1 | CATGTAAGTTCGACGAATTAATCGA (SEQ ID NO: 29) |
| | RT-Ca_Cd_Ct-F1 | CCACCAAAGGGTTGTGAC (SEQ ID NO: 23) |
| | RT-Ca_Ct-R3 | CAGCATCACCGGATTTGAC (SEQ ID NO: 24) |
| | RT-Cpar-R6 | CGGACTTGATGAATTTTGGTTCA (SEQ ID NO: 25) |
| | RT-Ca_Cd_Cp-T1-FAM-B1 | TGCTTGTAAATTCGACACTTTG (SEQ ID NO: 144) |
| Master Mix IV | SiT-Cgla-F8 | CGAACAATTGACTGAAGGTTTG (SEQ ID NO: 20) |
| | RT-Cgla-R7 | CGGACTTCAAGAACTTTGGAGA (SEQ ID NO: 21) |
| | RT-Cgla-T7-Fam-B1 | CTTGTAAGTTCGAAGAATTGTTGGA (SEQ ID NO: 22) |
| | TV.MAX.FP1 | GAAGATTCTGGCAAGATCAAGGA (SEQ ID NO: 17) |

TABLE 7b-continued

Non-selected master mixes for detection of VVC and trichomoniasis

| Master Mix ID | Primers and Probes | Primer and Probe Sequences (5'-3') |
|---|---|---|
| | TV.MAX.RP1 | ACGACAATGCAGCGGATGT (SEQ ID NO: 18) |
| | TV.MAX.D1-T-ROX-B2 | ATCCTCCGCAACTACCCACGCCA (SEQ ID NO: 19) |
| | RT-Ckru-F7 | GCAGCTTCCTTCAATGCTCAA (SEQ ID NO: 27) |
| | SiT-Ckru-R10 | ATCACCAGACTTGACGG (SEQ ID NO: 174) |
| | SiT-Ckru-T9-CFO-B1 | ATGTAAGTTCGACGAATTAATC (SEQ ID NO: 176) |
| | RT-Ca_Cd_Ct-F1 | CCACCAAAGGGTTGTGAC (SEQ ID NO: 23) |
| | RT-Ca_Ct-R3 | CAGCATCACCGGATTTGAC (SEQ ID NO: 24) |
| | RT-Ca_Cd_Cp-T1-FAM-B1 | TGCTTGTAAATTCGACACTTTG (SEQ ID NO: 144) |
| Master Mix V | SiT-Cgla-F8 | CGAACAATTGACTGAAGGTTTG (SEQ ID NO: 20) |
| | RT-Cgla-R7 | CGGACTTCAAGAACTTTGGAGA (SEQ ID NO: 21) |
| | RT-Cgla-T7-Fam-B1 | CTTGTAAGTTCGAAGAATTGTTGGA (SEQ ID NO: 22) |
| | TV.MAX.FP1 | GAAGATTCTGGCAAGATCAAGGA (SEQ ID NO: 17) |
| | TV.MAX.RP1 | ACGACAATGCAGCGGATGT (SEQ ID NO: 18) |
| | TV.MAX.D1-T-ROX-B2 | ATCCTCCGCAACTACCCACGCCA (SEQ ID NO: 19) |
| | RT-Ckru-F7 | GCAGCTTCCTTCAATGCTCAA (SEQ ID NO: 27) |
| | SiT-Ckru-R10a | ATCACCAGACTTGACAG (SEQ ID NO: 28) |
| | SiT-Ckru-T10-CFO-B1 | AGTCTGTTGAAGACCATCCA (SEQ ID NO: 175) |
| | RT-Ca_Cd_Ct-F1 | CCACCAAAGGGTTGTGAC (SEQ ID NO: 23) |
| | RT-Ca_Ct-R3 | CAGCATCACCGGATTTGAC (SEQ ID NO: 24) |
| | RT-Ca_Cd_Cp-T1-FAM-B1 | TGCTTGTAAATTCGACACTTTG (SEQ ID NO: 144) |

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above.

Whenever a range of values is provided herein, the range is meant to include the starting value, the ending value, each individual value, or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like. As another example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method to detect vulvovaginal candidiasis (VVC)-associated *Candida* species and *Trichomonas vaginalis* in a biological sample, wherein the VVC-associated *Candida* species is selected from the group consisting of *Candida glabrata, Candida albicans, Candida tropicalis, C. dubliniensis, C. parapsilosis, Candida krusei*, and a combination thereof, comprising:
   contacting said biological sample with a plurality of pairs of primers, wherein the plurality of pairs of primers comprises:
   at least one pair of primers capable of hybridizing to the tef1 gene of *Candida glabrata*, wherein each primer in said at least one pair of primers comprises a sequence of SEQ ID NO: 20 or SEQ ID NO: 21 or a sequence differing by only one nucleotide mismatch relative to SEQ ID NO: 20 or SEQ ID NO: 21;
   at least one pair of primers capable of hybridizing to the tef1 gene of at least one of *Candida albicans, Candida tropicalis, C. dubliniensis*, and *C. parapsilosis*, wherein each primer in said at least one pair of primers comprises a sequence of SEQ ID NO: 23, SEQ ID NO: 24, or SEQ ID NO: 25, or a sequence differing by only one nucleotide mismatch relative to SEQ ID NO: 23, SEQ ID NO: 24, or SEQ ID NO: 25;
   at least one pair of primers capable of hybridizing to the tef1 gene of *Candida krusei*, wherein each primer in said at least one pair of primers comprises a sequence of SEQ ID NO: 27 or SEQ ID NO: 28, or a sequence differing by only one nucleotide mismatch relative to SEQ ID NO: 27 or SEQ ID NO: 28; and
   at least one pair of primers capable of hybridizing to the AP-65 gene of *Trichomonas vaginalis*, wherein each primer in said at least one pair of primers comprises a sequence of SEQ ID NO: 17 or SEQ ID NO: 18, or a sequence differing by only one nucleotide mismatch relative to SEQ ID NO: 17 or SEQ ID NO: 18; and
   generating amplicons of the tef1 sequences of the *Candida* species and/or amplicons of the AP-65 gene sequence of *Trichomonas vaginalis* from said biological sample, if said sample comprises one or more of the VVC-associated *Candida* species and/or *Trichomonas vaginalis*; and
   determining the presence or amount of one or more amplified products as an indication of the presence of VVC-associated *Candida* species and *Trichomonas vaginalis* in said biological sample.

2. The method of claim 1, wherein said biological sample is a clinical sample.

3. The method of claim 1, wherein said biological sample is collected from the urethra, penis, anus, throat, cervix, or vagina.

4. The method of claim 1, wherein said biological sample is a vaginal sample.

5. The method of claim 1, wherein the plurality of pairs of primers comprises a first primer comprising the sequence of SEQ ID NO: 20, a second primer comprising the sequence of SEQ ID NO: 21, a third primer comprising the sequence of SEQ ID NO: 23, a fourth primer comprising the sequence of SEQ ID NO: 24, a fifth primer comprising the sequence of SEQ ID NO: 25, a sixth primer comprising the sequence of SEQ ID NO: 27, a seventh primer comprising the sequence of SEQ ID NO: 28, an eighth primer comprising the sequence of SEQ ID NO: 17, and a ninth primer comprising the sequence of SEQ ID NO: 18.

6. The method of claim 1, wherein
   the pair of primers capable of hybridizing to the tef1 gene of *Candida glabrata* is SEQ ID NOs: 20 and 21;
   the at least one pair of primers capable of hybridizing to the tef1 gene of at least one of *Candida albicans, Candida tropicalis, C. dubliniensis*, and *C. parapsilosis* are:
   a) SEQ ID NOs: 23 and 24,
   b) SEQ ID NOs: 23 and 25, or
   c) a combination thereof;
   the pair of primers capable of hybridizing to the tef1 gene of *Candida krusei* consists of SEQ ID NOs: 27 and 28; and
   the pair of primers capable of hybridizing to the 16S rRNA gene of *Trichomonas vaginalis* is SEQ ID NOs: 17 and 18.

7. The method of claim 1, wherein said amplification generating amplicons of the tef1 sequences of the *Candida* species and/or amplicons of the AP-65 gene sequence of *Trichomonas vaginalis* from said biological sample is carried out using a method selected from the group consisting of polymerase chain reaction (PCR), ligase chain reaction (LCR), loop-mediated isothermal amplification (LAMP), strand displacement amplification (SDA), replicase-mediated amplification, Immuno-amplification, nucleic acid sequence based amplification, self-sustained sequence replication, rolling circle amplification, and transcription-mediated amplification (TMA).

8. The method of claim 7, wherein said PCR is real-time PCR.

9. The method of claim 1, wherein each primer comprises exogenous nucleotide sequence which allows post-amplification manipulation of amplification products without a significant effect on amplification itself.

10. The method of claim 1, wherein each primer is flanked by complementary sequences comprising a fluorophore at the 5' end, or a fluorescence quencher at the 3' end, or both.

11. The method of claim 1, wherein determining the presence or amount of one or more amplified products comprises contacting the amplified products with a plurality of oligonucleotide probes, wherein each of the plurality of oligonucleotide probes comprises a sequence selected from the group consisting of SEQ ID NOs: 22, 26, 29, and 19, or a sequence differing by only one nucleotide mismatch relative to a sequence selected from the group consisting of SEQ ID NOs: 22, 26, 29, and 19.

12. The method of claim 11, wherein each of the plurality of oligonucleotide probes comprises a sequence selected from the group consisting of SEQ ID NOs: 22, 26, 29, and 19.

13. The method of claim 12, wherein each of the plurality of oligonucleotide probes consists of a sequence selected from the group consisting of SEQ ID NOs: 22, 26, 29, and 19.

14. The method of claim 11, wherein at least one of the plurality of oligonucleotide probes comprises a fluorescence emitter moiety, a fluorescence quencher moiety, or both.

15. A composition for the detection of vulvovaginal candidiasis (VVC)-associated *Candida* species and *Trichomonas vaginalis* in a biological sample, wherein the VVC-associated *Candida* species comprises *Candida glabrata, Candida albicans, Candida tropicalis, C. dubliniensis, C. parapsilosis, Candida krusei*, comprising:
   at least one pair of primers capable of hybridizing to the tef1 gene of *Candida glabrata*, wherein each primer in said at least one pair of primers comprises a sequence of SEQ ID NO: 20 or SEQ ID NO: 21 or a sequence differing by only one nucleotide mismatch relative to SEQ ID NO: 20 or SEQ ID NO: 21;

at least one pair of primers capable of hybridizing to the tef1 gene of at least one of *Candida albicans, Candida tropicalis, C. dubliniensis*, and *C. parapsilosis*, wherein each primer in said at least one pair of primers comprises a sequence of SEQ ID NO: 23, SEQ ID NO: 24, or SEQ ID NO: 25, or a sequence differing by only one nucleotide mismatch relative to SEQ ID NO: 23, SEQ ID NO: 24, or SEQ ID NO: 25;

at least one pair of primers capable of hybridizing to the tef1 gene of *Candida krusei*, wherein each primer in said at least one pair of primers comprises a sequence of SEQ ID NO: 27 or SEQ ID NO: 28, or a sequence differing by only one nucleotide mismatch relative to SEQ ID NO: 27 or SEQ ID NO: 28;

at least one pair of primers capable of hybridizing to the AP-65 gene of *Trichomonas vaginalis*, wherein each primer in said at least one pair of primers comprises a sequence of SEQ ID NO: 17 or SEQ ID NO: 18, or a sequence differing by only one nucleotide mismatch relative to SEQ ID NO: 17 or SEQ ID NO: 18; and a plurality of oligonucleotide probes, wherein each of the plurality of oligonucleotide probes comprises a sequence selected from the group consisting of SEQ ID NOs: 22, 26, 29, and 19, or a sequence differing by only one nucleotide mismatch relative to a sequence selected from the group consisting of SEQ ID NOs: 22, 26, 29, and 19, and wherein each of the plurality of oligonucleotide probes comprises a fluorescence emitter moiety and a fluorescence quencher moiety.

16. The composition of claim 15, wherein the at least one pair of primers capable of hybridizing to the tef1 gene of *Candida glabrata* comprises a primer comprising the sequence of SEQ ID NO: 20 and a primer comprising the sequence of SEQ ID NO: 21;

the at least one pair of primers capable of hybridizing to the tef1 gene of at least one of *Candida albicans, Candida tropicalis, C. dubliniensis*, and *C. parapsilosis* comprises a primer comprising the sequence of SEQ ID NO: 23, a primer comprising the sequence of SEQ ID NO: 24, and a primer comprising the sequence of SEQ ID NO: 25;

the at least one pair of primers capable of hybridizing to the tef1 gene of *Candida krusei* comprises a primer comprising the sequence of SEQ ID NO: 27 and a primer comprising the sequence of SEQ ID NO: 28; and the at least one pair of primers capable of hybridizing to the AP-65 gene of *Trichomonas vaginalis* comprises a primer comprising the sequence of SEQ ID NO: 17 and a primer comprising the sequence of SEQ ID NO: 18.

17. The composition of claim 15, wherein each of the plurality of oligonucleotide probes comprises a sequence selected from the group consisting of SEQ ID NOs: 22, 26, 29, and 19.

18. The composition of claim 17, wherein each of the plurality of oligonucleotide probes consists of a sequence selected from the group consisting of SEQ ID NOs: 22, 26, 29, and 19 a fluorescence emitter moiety, and a fluorescence quencher moiety.

19. The composition of claim 15, comprising a DNA polymerase, bivalent cations, monovalent cation potassium ions, or a combination thereof.

* * * * *